US012662450B2

(12) United States Patent
Akazawa et al.

(10) Patent No.: US 12,662,450 B2
(45) Date of Patent: Jun. 23, 2026

(54) ONIUM SALT AND PHOTOACID GENERATOR

(71) Applicant: SAN-APRO LTD., Kyoto (JP)

(72) Inventors: Yoshihiko Akazawa, Kyoto (JP); Tomohito Kizu, Kyoto (JP); Ryosuke Takahashi, Kyoto (JP); Yuji Nakamura, Kyoto (JP); Hideki Kimura, Kyoto (JP)

(73) Assignee: SAN-APRO LTD., Kyoto (JP)

( * ) Notice: Subject to any disclaimer, the term of this patent is extended or adjusted under 35 U.S.C. 154(b) by 484 days.

(21) Appl. No.: 17/641,943

(22) PCT Filed: May 7, 2021

(86) PCT No.: PCT/JP2021/017492

§ 371 (c)(1),
(2) Date: Mar. 10, 2022

(87) PCT Pub. No.: WO2021/251035

PCT Pub. Date: Dec. 16, 2021

(65) Prior Publication Data

US 2022/0315530 A1 Oct. 6, 2022

(30) Foreign Application Priority Data

Jun. 12, 2020 (JP) ................................ 2020-102020

(51) Int. Cl.

*C07C 381/12* (2006.01)
*C07C 25/18* (2006.01)
*C07F 9/535* (2006.01)
*G03F 7/004* (2006.01)
*G03F 7/038* (2006.01)
*G03F 7/039* (2006.01)

(52) U.S. Cl.

CPC ............ *C07C 381/12* (2013.01); *C07C 25/18* (2013.01); *C07F 9/535* (2013.01); *G03F 7/004* (2013.01); *G03F 7/0045* (2013.01); *G03F 7/0382* (2013.01); *G03F 7/039* (2013.01); *G03F 7/0392* (2013.01)

(58) Field of Classification Search

CPC ...... G03F 7/039; G03F 7/0045; G03F 7/0392; G03F 7/004; G03F 7/0382

See application file for complete search history.

(56) References Cited

U.S. PATENT DOCUMENTS

| | | | | |
|---|---|---|---|---|
| 6,723,483 | B1 | 4/2004 | Oono et al. | |
| 7,094,328 | B2 * | 8/2006 | Ignatyev .............. | B01J 31/0288 429/324 |
| 2002/0045122 | A1 | 4/2002 | Iwasa et al. | |
| 2004/0171879 | A1 | 9/2004 | Ignatyev et al. | |
| 2007/0225458 | A1 | 9/2007 | Kimura et al. | |
| 2009/0163723 | A1 * | 6/2009 | Kimura ................. | C07C 381/12 558/202 |
| 2011/0300482 | A1 * | 12/2011 | Suzuki .................. | C07C 381/12 430/326 |
| 2017/0306198 | A1 | 10/2017 | Newcomb et al. | |
| 2018/0373145 | A1 * | 12/2018 | Shiraishi ............. | C09B 23/0066 |
| 2021/0147352 | A1 | 5/2021 | Nakao et al. | |

FOREIGN PATENT DOCUMENTS

| | | |
|---|---|---|
| CN | 107870517 | 4/2018 |
| JP | 2001-354669 | 12/2001 |
| JP | 2002-193925 | 7/2002 |
| JP | 2004-189673 | 7/2004 |
| JP | 2004-533473 | 11/2004 |
| JP | 2012-27290 | 2/2012 |
| JP | 2015-86371 | 5/2015 |
| JP | 2016-42127 | 3/2016 |
| JP | 2019-73470 | 5/2019 |
| JP | 2019-203100 | 11/2019 |
| WO | 2005/116038 | 12/2005 |
| WO | 2019/225185 | 11/2019 |

OTHER PUBLICATIONS

N.V. Ignat' ev, et al., "New ionic liquids with tris(perfluoroalkyl)trifluorophosphate (FAP) anions", Journal of Fluorine Chemistry, 2005, vol. 126, pp. 1150-1159.

International Search Report issued Jul. 6, 2021 in corresponding International (PCT) Patent Application No. PCT/JP2021/017492.

* cited by examiner

*Primary Examiner* — Mark F. Huff
(74) *Attorney, Agent, or Firm* — Wenderoth, Lind & Ponack, L.L.P.

(57) ABSTRACT

Provided is an onium salt functioning as a photoacid generator. The photoacid generator can provide a chemically amplifiable photoresist composition when it is combined with a resin component whose solubility in alkali is increased by the action of an acid generated by active energy ray irradiation such as Light or electron beam irradiation. The present invention relates to an onium salt represented by the formula (1), containing an anion structure with a proportion of a facial isomer in a total of the facial isomer and a meridional isomer being 15.0% by weight or lower.

$$[(R^2)_{n+1}\text{-}E]^+[(R^1)_3(F)_3P]^- \quad (1)$$

3 Claims, No Drawings

ONIUM SALT AND PHOTOACID GENERATOR

TECHNICAL FIELD

The present invention relates to a novel onium salt and a novel onium salt-type photoacid generator. Specifically, the present invention relates to a photoacid generator suitable as a resin composition for a chemically amplifiable resist used for semiconductor pattern formation.

BACKGROUND ART

Photoacid generators have been known which generate acids through active energy ray irradiation such as light or electron beam irradiation. Furthermore, these photoacid generators have been widely known as photoacid generators for resists (Patent Literatures 1 and 2).

The Descriptions of these literatures disclose sulfonate, $BF_4^-$, $PF_6^-$, $AsF_6^-$, and $SbF_6^-$ as anions. In the resist material field, especially in the semiconductor resist field, use of $AsF_6^-$ and $SbF_6^-$ is avoided from the viewpoint of the toxicity of As and Sb. On the other hand, $BF_4^-$ and $PF_6^-$ are not useful because of their weak acid strength. Furthermore, Patent Literature 3 discloses a special phosphorus-type type. Yet, this also does not exhibit sufficient sensitivity. Patent Literature 4 discloses a method for producing such a special phosphorus-type. Yet, even with this method, no useful photoacid generator has been achieved.

CITATION LIST

Patent Literature

Patent Literature 1: JF 2002-193925 A
Patent Literature 2: JF 2001-354669 A
Patent Literature 3: WO 2005/116038
Patent Literature 4: JP 2004-533473 T

SUMMARY OF INVENTION

Technical Problem

In response to such problems, the present inventors have found that an onium salt having a specific anion structure in which stereoisomers are controlled within certain ranges provides a resist material with a specific high sensitivity, and have completed the present invention.

Solution to Problem

The present inventors synthesized an onium salt represented by the formula (1), containing an anion structure with a proportion of a facial isomer in a total of the facial isomer and a meridional isomer being 15.0% by weight or lower, and found that such an onium salt is suitable for the above purpose.

$$[(R^2)_{n+1}\text{-}E]^+[(R^1)_3(F)_3P]^- \quad (1)$$

In the formula (1), $R^1$ is a halogen-substituted C1-C18 alkyl group or a C6-C18 (excluding the carbon number of the following substituents) aryl group, with at least one hydrogen in the aryl group being optionally replaced by a C1-C18 alkyl group, a halogen atom, a halogen-substituted C1-C8 alkyl group, a C2-C18 alkenyl group, or a C2-C18 alkynyl group; E is any one of elements of groups 15 to 17 (IUPAC Notation) with a valence of n; n is an integer of 1 to 3; and $R^2$ is an organic group attached to the element E, with the number of $R^2$s being n+1, these $R^2$s being the same as or different from each other, and two or more $R^2$s being optionally attached to each other directly or with —O—, —S—, —SO—, —$SO_2$—, —NH—, —CO—, —COO—, —CONH—, an alkylene group, or a phenylene group in between to form a ring structure containing the element E.

Advantageous Effects of Invention

The onium salt of the present; invention functions as a photoacid generator, and the photoacid generator can provide a chemically amplifiable photoresist composition when it is combined with a resin component whose solubility in alkali is increased by the action of an acid generated by active energy ray irradiation such as light or electron beam irradiation. The onium salt of the present invention is specifically effective when used for such an application.

In other words, a chemically amplifiable positive photoresist composition and a chemically amplifiable negative photoresist composition which contain an acid generator containing the onium salt of the present invention can form a highly sensitive resist (i.e., enable pattern formation with a lower exposure than conventional ones). Furthermore, the chemically amplifiable positive photoresist composition and the chemically amplifiable negative photoresist composition of the present invention form good resist patterns.

DESCRIPTION OF EMBODIMENTS

Embodiments of the present invention are described in detail below.

The onium salt of the present invention is represented by the following formula (1).

The onium salt of the present invention is an onium salt represented by the formula (1), containing an anion structure with a proportion of a facial isomer in a total of the facial isomer and a meridional isomer, being.

$$[(R^2)_{n+1}\text{-}E]^+[(R^1)_3(F)_3P]^- \quad (1)$$

In the formula (1), $R^1$ is a halogen-substituted C1-C18 alkyl group or a C6-C13 (excluding the carbon number of the following substituents) aryl group, with at least one hydrogen in the aryl group being optionally replaced by a C1-C18 alkyl group, a halogen atom, a halogen-substituted C1-C8 alkyl group, a C2-C19 alkenyl group, or a C2-C18 alkynyl group; E is any one of elements of groups 15 to 17 (IUPAC Notation) with a valence of n; n is an integer of 1 to 3; and $R^2$ is an organic group attached to the element E, with the number of $R^2$s being n+1, these $R^2$s being the same as or different from each other, and two or more $R^2$s being optionally attached to each other directly or with —O—, —S—, —SO—, —$SO_2$—, —NH—, —CO—, —COO—, —CONH—, an alkylene group, or a phenylene group in between to form a ring structure containing the element E.

In an anion (B) of the onium salt (A) of the present invention, P is a phosphorus atom and F is a fluorine atom. $R^1$ is a halogen-substituted C1-C18 alkyl group or a C6-C18 (excluding the carbon number of the following substituents) aryl group. At least one hydrogen in the aryl group is optionally replaced by a C1-C18 alkyl group, a halogen atom, a halogen-substituted C1-C8 alkyl group, a C2-C18 alkenyl group, or a C2-C18 alkynyl group.

The anion (B) has a structure in which P serves as a central element, and three F atoms and three $R^1$ groups for a total of six are coordinated to P. For this structure, two isomers are present: a facial isomer in which the same ligands are in a cis position and a meridional isomer in which the sane ligands are in the same plane.

When the onium salt (A) functions as an acid generator, the anion (B) with a proton added thereto functions as an acid. For this reason, controlling the ratio between the two isomers is an extremely important factor. The proportion of the facial isomer in a total of the two isomers, the facial isomer and the meridional isomer, is controlled to 15.0% by weight or lower so that a remarkably highly sensitive resist (i.e., enable pattern formation with a lower exposure than conventional ones) can be prepared. The proportion of the facial isomer in a total of the two isomers, the facial isomer and the meridional isomer, is more preferably 0.1 to 15.0% by weight, most preferably 0.5 to 10.0% by weight.

$R^1$ is a halogen-substituted C1-C16 alkyl group or a C6-C18 (excluding the carbon number of the following substituents) aryl group. At least one hydrogen in the aryl group is optionally replaced by a C1-C18 alkyl group, a halogen atom, a halogen-substituted C1-C8 alkyl group, a C2-C18 alkenyl group, or a C2-C18 alkynyl group. Examples of these substituents are the same as the examples of $R^2$ described later. Of these examples, a perfluoroalkyl group and a fluorine-substituted phenyl group are preferred. Specifically, a pentafluoroethyl group, a heptafluoro-n-propyl group, a nonafluoro-n-butyl group, a heptafluoro-i-propyl group, a trifluoromethyl group, and the like are more preferred.

To control the ratio between the two isomers which are a facial isomer and a meridional isomer, the polarity of the solvent, the amounts or concentrations of the solvent and substance, and the reaction temperature are optimized when the precursor phosphorane ($(R^1)_3(F)_2P$) reacts with a fluorinating agent, tor example. Thus, desired isomers can be synthesized. Examples of the fluorinating agent include hydrogen fluoride and metal fluorides (sodium fluoride and potassium fluoride).

A cation (C) of the onium salt (A) is the cation part of the formula (1), and E is any one of elements of groups 15 to 17 (IUPAC Notation) with a valence of n; n is an integer of 1 to 3; and $R^2$ is an organic group attached to the element E, with the number of $R^2$s being n+1, these $R^2$s being the same as or different, from each other, and two or more $R^2$s being optionally attached to each other directly ox with —O—, —S—, —SO—, —$SO_2$—, —NH—, —CO—, —COO—, —CONH—, an alkylene group, or a phenylene group in between to form a ring structure containing the element E.

Specific examples of the element E include N, O, F, P, S, Cl, As, Se, Br, Sb, Te, and I. Preferred among these are S, I, N, and P. The corresponding cations (C) are sulfonium, iodonium, ammonium, and phosphonium. Still more preferred are S and I. The corresponding cations (C) are sulfonium and iodonium.

$R^2$s are same as or different from each other and are each an organic group attached to the element E. Examples of $R^2$ include a C1-C18 alkyl group, a C2-C18 alkenyl group, and a C6-C18 aryl group. The aryl group may further be substituted with a C1-C18 alkyl group, a C2-C18 alkenyl group, a C6-C18 aryl group, a nitro group, a hydroxy group, a cyano group, an alkoxy or aryloxy-group represented by —$OR^5$, an alkylthio or arylthio group represented by —$SR^6$, an acyl group represented by $R^7$CO—, an acyloxy group represented by $R^8$COO—, an amino group represented by —$NF^9R^{10}$, or a halogen atom.

Examples of the C1-C18 alkyl group for $R^2$ include linear alkyl groups (e.g., methyl, ethyl, n-propyl, n-butyl n-pentyl, n-octyl, n-decyl, n-dodecyl, n-tetradecyl, n-hexadecyl, and n-octadecyl), branched alkyl groups (e.g., isopropyl, isobutyl, sec-butyl, tert-butyl, isopentyl, neopentyl, tert-pentyl, isohexyl, 2-ethylhexyl, and 1,1,3,3-tetramethylbutyl), cycloalkyl groups (e.g., cyclopropyl, cyclobutyl, cyelopentyl, and cyclohexyl), crosslinked cyclic alkyl groups (e.g., norbornyl, adamantyl and pinanyl), and arylalkyl groups (e.g., benzyl, naphthylmethyl, phenethyl, benzhydryl, and phenacyl).

Examples of the C2-C18 alkenyl group for $R^2$ include linear or branched alkenyl groups (e.g., vinyl, allyl, 1-propenyl, 2-propenyl, 1-butenyl, 2-butenyl, 3-butenyl, 1-methyl-1-propenyl, 1-methyl-2 propenyl, 2-methyl-1-propenyl, and 2-methyl-2-propenyl), cycloalkenyl groups (e.g., 2-cyclohexenyl and 3-cyclohexenyl), and arylalkenyl groups (e.g., styryl and cinnamyl).

Examples of the C6-C18 (excluding the carbon number of the following substituents) aryl group for $R^2$ include monocyclic aryl groups (e.g., phenyl), fused polycyclic aryl groups (e.g., naphthyl, anthracenyl, phenanthrenyl, anthraquinolyl, fluorenyl, and naphthoquinolyl), and aromatic heterocyclic hydrocarbon groups (e.g., monocyclic heterocycles such as thienyl, furanyl, pyranyl, pyrrolyl, oxazolyl, thiazolyl, pyridyl, pyrimidyl, and pyrazinyl, and fused polycyclic heterocycles such as indolyl, benzofuranyl isobenzofuranyl, benzothienyl, isobenzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, coumarinyl, dibenzothienyl, xanthonyl, thioxanthonyl, and dibenzofuranyl).

Examples of the aryl group include, in addition to the above aryl groups, an aryl group, with at least one hydrogen in the aryl group being optionally replaced by a C1-C18 alkyl group, a C2-C18 alkenyl group, a C6-C18 aryl group, a nitro group, a hydroxy group, a cyano group, an alkoxy or aryloxy group represented by —$OR^5$, an alkylthio or arylthio group represented by —$SR^6$, an acyl group represented by $R^7$CO—, an acyloxy group represented by $R^8$COO—, an amino group represented by —$NR^9R^{10}$, or a halogen atom.

$R^5$ to $R^{10}$ in the alkoxy group represented by —$OR^5$, the alkylthio group represented by —$SR^6$, the acyl group represented by $R^7$CO—, the acyloxy group represented by $R^8$COO—, and the amino group represented by —$NR^9R^{10}$ among the above-listed substituents are each a C1-C8 alkyl group, for example. Specific examples thereof include the C1-C8 alkyl groups among the above-listed alkyl groups.

$R^5$ to $R^{10}$ in the aryloxy group represented by —$OR^5$, the arylthio group represented by —$SR^6$, the acyl group represented by $R^7$CO—, the acyloxy group represented by $R^8$COO—, and the amino group represented by —$NR^9R^{10}$ among the above-listed substituents are each a C6-C18 aryl group, for example. Specific examples thereof include the above-listed C6-C18 aryl groups.

Examples of the alkoxy group for —$OR^5$ include methoxy, ethoxy, n-propoxy, iso-propoxy, n-butoxy, sec-butoxy, tert-butoxy, n-pentoxy, iso-pentoxy, neo-pentoxy, and 2-methylbutoxy.

Examples of the aryloxy group for —$OR^5$ include phenoxy and naphthoxy.

Examples of the alkylthio group for —$SR^6$ include methylthio, ethylthio, butylthio, hexylthio, and cyclohexylthio.

Examples of the arylthio group for —$SR^6$ include phenylthio, naphthylthio, biphenylthio, and 2-thioxanthonylthio.

Examples of the acyl group for $R^7$CO— include acetyl, propanoyl, butanoyl, pivaloyl, and benzoyl.

Examples of the acyloxy group for $R^8$COO— include acetoxy, butanoyloxy, and benzoyloxy.

Examples of the amino group for —$NR^9R^{10}$ include methylamino, ethylamino, propylamino, dimethylamino, diethylamino, methylethylamino, dipropylamino, dipropylamino, and piperidino.

Examples of the halogen atom include a fluorine atom, a chlorine atom, a bromine atom, and an iodine atom.

$R^2$ is preferably a C1-C18 alkyl group, a C6-C18 aryl group, or a C6-C18 aryl group substituted with a nitro group, a hydroxy group, a C1-C18 alkyl group, an alkoxy group represented by —$OR^5$, an arylthio group represented by —$SR^6$, an acyl group represented by $R^7CO$—, an acyloxy group represented by $R^8COO$—, or a chlorine atom.

$R^2$ is more preferably a C1-C18 alkyl group, a phenyl group, or a phenyl group substituted with a hydroxy group, a C1-C18 alkyl group, an alkoxy group represented by —$OR^5$, an arylthio group represented by —$SR^6$, an acetyl group, a benzoyl group, or an acetoxy group.

Two or more $R^2$s may be attached to each other directly or with —O—, —S—, —SO—, —$SO_2$—, —NH—, —CO—, —COO—, —CONH—, an alkylene group, or a phenylene group in between to form a ring structure containing the element E.

The following describes specific examples of the cation (C).

Specific examples of the ammonium ion include tetraalkylammonium ions such as tetramethylammonium, ethyltrimethylammonium, diethyldimethylammonium, triethylmethylammonium, and tetraethylammonium ions; pyrrolidinium ions such as N,N-dimethylpyrroidinium, N-ethyl-N-methylpyrrolidinium, and N, N-diethylpyrrolidinium ions; imidazolinium ions such as N,N'-dimethylimidazolinium N,N'-diethylimidazolinium, N-ethyl-N'-methylimidazolinium, 1,3,4-trimethylimidazolinium, and 1,2,3,4-tetramethylimidazolinium, ions; tetrahydropyrimidium ions such as an N,N'-dimethyltetrahydropyrimidinium ion; morpholinium ions such as a N,N'-dimethylmorpholiniumion; piperidinium ions such as a N,N'-diethylpiperidinium ion; pyridinium ions such as N-methylpyridinium, N-benzylpyridinium, and N-phenacylpyridinium ions; imidazolium ions such as a N,N'-dimethymidazolium ion; quinolium ions such as N-methylquindium, N-henzylquinolium and N-phenacylquindium ions; isoquindium ions such as a N-methylisoquinolium ion; thiazonium ions such as benzylbenzothiazonium and phenacylbenzothiazonium ions; and acrydium ions such as benzylacrydium and phenacylacrydium ions.

Specific examples of the phosphonium ion include tetraarylphosphonium ions such as tetraphenylphosphonium, tetra-p-tolylphosphonium, tetrakis(2-methoxyphenyl)phosphonium, tetrakis(3-methoxyphenyl)phosphorium, and tetrakis(4-methoxyphenyl)phosphonium ions; triarylphosphonium ions such as triphenylbenzylphosphonium, triphenylphenacylphosphonium, triphenylmethylphosphonium, and triphenylbutylphosphonium ions; and tetraalkylphosphonium ions such as triethylbenzylphosphonium, tributylbenzylphosphonium, tetraethylphosphonium, tetrabutylphosphonium, tetrahexylphosphonium, triethyophenacylphosphonium, and tributylphenacylphosphonium ions.

Specific examples of the sulfonium ion include triarylsultonium ions such as triphenylsulfonium, tri-p-tolylsulfonium, tri-o-tolylsulfonium, tris(4-methoxyphenyl)sulfonium, 1-naphthyldiphenylsulfonium, 2-naphthyldiphenylsulfonium, tris(4-fluorophenyl)sulfonium, tri-1-naphthylsulfonium, tri-2-naphthylsulfonium, tris (4-hydroxyphenyl) sulfonium, 4-(phenylthio)phenyldiphenylsulfonium, 4-(p-tolylthio)phenyldi-p-tolylsulfonium, 4-(4-methoxyphenylthio)phenyl-bis(4-methoxyphenyl) sulfonium, 4-(phenylthio)phenyl-bis(4-fluorophenyl)sulfonium, 4-(phenylthio)phenyl-bis(4-methoxyphenyl)sulfonium, 4-(phenylthio)phenyldi-p-tolylsulfonium, [4-(4-biphenylylthio)phenyl]-4-biphenylylphenylsulfonium, [4-(2-thioxanthonylthio)phenyl]diphenylsulfonium, bis[4-(diphenylsulfonio)phenyl]sulfide, bis[4-{bis[4-(2-hydroxyethoxy)phenyl]sulfonio}phenyl]sulfide, bis{4-[bis (4-fluorophenyl) sulfonio]phenyl}sulfide, bis{4-[bis(4-methylphenyl) sulfonio]phenyl}sulfide, bis{4-[bis(4-methoxyphenyl) sulfonio]phenyl}sulfide, 4-(4-benzoyl-2-chlorophenylthio)phenyl-bis(4-fluorophenyl) sulfonium, 4-(4-benzoyl-2-chlorophenylthio)phenyldiphenylsulfonium 4-(4-benzeylphenylthio)phenyl-bis(4-fluorophenyl) sulfonium, 4-(4-benzoylphenylthio)phenyldiphenylsulfonium, 7-isopropyl-9-oxo-10-thia-9,10-dihydroanthracen-2-yl-di-p-tolylsulfonium, 7-isopropyl-9-oxo-10-thia-9,10-dihydroanthrace-2-yl-diphenylsulfonium, 2-[(di-p-tolyl) sulfonio]thioxanthone, 2-[(diphenyl) sulfonio]thioxanthone, 4-(9-oxo-9H-thioxanthen-2-yl)thiophenyl-9-oxo-9H-thioxanthen-2-yl-phenylsulfonium, 4-[4-(4-tert-butylbenzoyl) phenylthio]phenyldi-p-tolylsulfonium, 4-[4-(4-tert-butylbenzoyl)phenylthio]phenyldiphenylsulfonium, 4-[4-(benzoylphenylthio)]phenyldi-p-tolylsulfonium, 4-[4-(benzoylphenylthio)]phenyldiphenylsulfonium, 5-(4-methoxyphenyl) thianthrenium, 5-phenylthianthrenium, 5-tolylthianthrenium, 5-(4-ethoxyphenyl) thianthrenium, and 5-(2,4,6-trimethylphenyl)thianthrenium ions; diarylsulfonium ions such as diphenylphenacylsulfonium, diphenyl-4-nitrophenacylsulfonium, diphenylbenzylsulfonium, and diphenylmethylsulfonium ions; monoarylsulfonium ions such as phenylmethylbenzylsulfonium, 4-hydroxyphenylmethylbenzylsulfonium, 4-methoxyphenylmethylbenzylsulfonium, 4-acetoxyphenylmethylbenzylsulfonium, 4-acetoxyphenyldimethylsulfonium, 4-hydroxyphenyl(1-naphthylmethyl)methylsulfonium, 2-naphthylmethylbenzylsulfonium, 4-hydroxyphenyl (4-nitrobenzymethylsulfonium, 2-naphthylmethyl(1-ethoxycarbonyl)ethylsulfonium, phenylmethylphenacylsulfonium, 4-hydroxyphenylmethylphenacylsulfonium, 4-methoxyphenylmethylphenacylsulfonium, 4-acatoxyphenylmethylphenacylsulfonium, 2-naphthylmethylphenacylsulfonium, 2-naphthyloctadecylphenacylsulfonium, and 9-anthracenylmethylphenacylsulfonium ions; and trialkylsulfonium ions such as dimethylphenacylsulfonium, phenacyltetrahydrothiophenium, dimethylbenzylsulfonium, benzyltetrahydrothiophenium, and octadecylmethylphenacylsulfonium ions.

Specific examples of the iodonium ion include diphenyliodonium, di-p-tolyliodonium, di(4-tert-butylphenyl)iodonium, di(4-dodecylphenyl)iodonium, di(4-methoxyphenyl) iodonium, (4-octyloxyphenyl)phenyliodonium, di(4-decyloxyphenyl)iodonium, 4-(2-hydroxytetradecyloxy) phenylphenyliodonium, 4-isopropylphenyl(p-tolyl) iodonium, phenyl(2,4,6-trimethoxyphenyl)iodonium, and 4-isobutylphenyl(p-tolyl)iodonium.

The onium salt represented by the formula (1) of the present invention can be produced by double decomposition. The double decomposition is described in, for example. Shin Jikken Kagaku Koza, Vol. 14-I (1978, Maruzen), p. 448; Advance in Polymer Science, 62, 1-48 (1984); Shin Jikken Kagaku Koza, Vol. 14-III (1978, Maruzen), pp. 1838-1846; Yuki Iqu Kagaku (Organic Chemistry of Sulfur) (Synthesis Reaction Edition, 1982, Kagaku Dojin), Chapter 6, pp. 237-280; Nippon Kagaku Zassbi, 87, (5), 74 (1966); JP S64-45357 A, JP sex-212854 A, JP S61-10C557 A, JP 85-4996 A, JP H7-82244 A, JP H7-82245 A, JP S5S-210904 A, and JP H6-184170 A. Specifically, the onium salt is produced as follows: A salt of an onium cation is produced with a halogen ion such as $F^-$, $Cl^-$, $Br^-$, or $I^-$; $OH^-$; $ClO_4^-$; a sulfonate ion such as $FSO_3^-$, $ClSO_3^-$, $CH_3SO_3^-$, $C_6H_5SO_3^-$, or $CF_3SO_3^-$; a sulfate ion such as $HSO_4^-$ or $SO_4^{2-}$; a carbonate ion such as $HCO_3^-$ or $CO_3^{2-}$; or a phosphate ion such as $H_2PO_4^-$, $HPO_4^{2-}$, or $PO_4^{3-}$, and the salt is added to a solution containing a solvent and an alkali metal salt, an alkaline earth metal salt, or a quaternary ammonium salt of the anion constituting the onium salt represented by the formula (1) for double decomposition. The solvent may be water or an organic solvent. Examples of the organic solvent include hydrocarbons (e.g., hexane, heptane, toluene, and xylene), cyclic ethers (e.g., tetrahydrofuran and dioxane), chlorine-based solvents (e.g., chloroform and dichloromethane), alcohols (e.g., methanol, ethanol, and isopropyl alcohol), ketones (e.g., acetone, methyl ethyl ketone, or methyl isobutyl ketone), nitriles (e.g., acetonitrile), and polar organic solvents (e.g., dimethylsulfoxide, dimethylformamide, and N-methylpyrrolidone). These solvents may be used alone or two or more of these may be used in combination.

The target onium salt thus produced separates in a crystalline or oily form. In the case of the oily form, the precipitated oily substance is separated from the organic solvent solution and the organic solvent contained in the oily substance is evaporated. In the case of the crystalline form, the precipitated solids are separated from the organic solvent solution and the organic solvent contained in the solids is evaporated. The target onium salt thus produced can be purified by methods such as recrystallization or washing with water or a solvent, if necessary.

The purification by recrystallization can be carried out by dissolving the target onium salt in a small amount of an organic solvent, and directly (or after condensation) adding a poor solvent to the organic solvent solution containing the target onium salt to precipitate the target onium salt, which is separated from the organic solvent. Examples of the poor solvent used herein include acyclic ethers (e.g., diethyl ether and dipropyl ether), esters (e.g., ethyl acetate and butyl acetate), aliphatic hydrocarbons (e.g., hexane and cyclohexane), and aromatic hydrocarbons (e.g., toluene and xylene). The purification may also be performed by utilizing the difference in solubility depending on the temperature. The purification can be performed by recrystallization (a method for utilizing the difference in solubility caused by cooling, a method for precipitating including adding a poor solvent, and the combination thereof). In order to obtain an oily onium salt (in other words, when crystallization does not occur), the oily onium salt can bis purified by washing with water or a poor solvent.

Before using the onium salt represented by the formula (1), it may be dissolved in a solvent that does not inhibit polymerization, crosslinking, deprotection reaction, and the like so that it is easily dissolved in a chemically amplifiable resist composition.

Examples of the solvent include: carbonates such as propylene carbonate, ethylene carbonate, 1,2-butylene carbonate, dimethyl carbonate, and diethyl carbonate; ketones such as acetone, methyl ethyl ketone, cyclchexanone methyl isoamyl ketone, and 2-heptanone; polyhydric alcohols and derivatives thereof, such as monomethyl ethers, monoethyl ethers, monopropyl ethers, monobutyl ethers, or monophenyl ethers of ethylene glycol, ethylene glycol monoacetate, diethylene glycol, diethylene glycol monoacetate, propylene glycol, propylene glycol monoacetate dipropylene glycol, and dipropylene glycol monoacetate; cyclic ethers such as dioxane; esters such as ethyl formate methyl lactate, ethyl lactate, methyl acetate, ethyl acetate, butyl acetate, methyl pyruvate, methyl acetoacetate, ethyl acetoacetate, ethyl pyruvate, ethyl ethoxyacetate, methyl methoxypropionate, ethyl ethoxypropionate, methyl 2-hydroxypropionate, ethyl 2-hydroxypropionate, ethyl 2-hydroxy-2-methylpropionate, methyl 2-hydroxy-3-methylbutanoate, 3-methoxybutyl acetate, and 3-methyl-3-methoxybutyl acetate; and aromatic hydrocarbons such as toluene and xylene.

When a solvent is used, the amount, of the solvent is preferably from 15 to 1000 parts by weight, more preferably from 30 to 500 parts by weight per 100 parts by weight of the onium salt represented by the formula (1) of the present invention. A single solvent may be used alone or two or more solvents may be used in combination.

The onium salt of the present invention is used as a photoacid generator and further mixed with various components to provide an energy ray-curable composition. The composition can provide a cured product when exposed to an energy ray.

The energy ray may be any energy ray having energy to induce the decomposition of the photoacid generator of the present invention. Preferred examples of the energy ray include energy rays in the ultraviolet to visible light region (wavelength: from about 100 to about 800 nm) applied from a low pressure-, medium pressure-, high pressure-, or ultra high pressure-mercury lamp, a metal halide lamp, an LED lamp, a xenon lamp, a carbon arc lamp, a fluorescent lamp, a semiconductor solid-state laser, an argon laser, a He—Cd laser, a KrF excimer laser, an ArF excimer laser, or an $F_2$ laser. Radiations with a high energy, such as electron beam or X-rays, may also be used as the energy ray.

The exposure time to an energy ray is influenced by the intensity of the energy ray or the permeability of the energy ray-curable composition to the energy ray. At room temperature (about 20° C. to 30° C.), exposure for about 0.1 to 10 seconds is enough. If the permeability to the energy ray is low or if the energy ray-curable composition is thick, for example, the time may preferably be extended. Most energy ray-curable compositions are cured by cationic polymerization in 0.1 seconds to several minutes after the exposure to an energy ray. Post-curing may optionally be performed by heating at a temperature of room temperature (about 20° C. to 30° C.) to 200° C. for several seconds to several hours after the exposure to the energy ray.

Specific applications of the energy ray-curable composition include positive resists (for connection terminals, wiring pattern formation, or the like for manufacturing electronic components such as circuit boards, CSF devices, and MEMS devices) and negative resists (permanent film materials such as surface protective films, interlayer insulating films, and planarizing films, of semiconductor devices and the like).

Examples of the chemically amplifiable resist materials include (1) a two-component chemically amplifiable positive resist containing, as essential components, a resin that can be made soluble in an alkaline developer by the action of an acid, and a photoacid generator; (2) a three-component chemically amplifiable positive resist containing, as essential components, a resin soluble in an alkaline developer, a dissolution inhibitor that can be made soluble in an alkaline developer by the action of an acid, and a photoacid generator; and (3) a chemically amplifiable negative resist containing, as essential components, a resin soluble in an alkaline developer, a crosslinking agent that can crosslink resin to make the resin insoluble in an alkaline developer when heated in the presence of an acid, and a photoacid generator.

The chemically amplifiable positive photoresist compositions (1) and (2) contain a resin component (F) whose solubility in alkali is increased by the action of an acid generated when the onium salt (A) of the present invention, which is a compound generating art acid when exposed to light or radiation, functions as an acid generator.

The amount of the onium salt (A) in the solids of the chemically amplifiable positive photoresist composition is preferably from 0.05 to 5% by weight.

Resin Component (F) Whose Solubility in Alkali is Increased by the Action of an Acid The "resin (F) whose solubility in alkali is increased by the action of an acid" (hereinafter, referred to as "component (F)") in the chemically amplifiable positive photoresist composition of the present invention is a resin selected from the group consisting of a novolac resin (F1), a polyhydroxystyrene resin (F2), and an acrylic resin (F3), or a mixture or a copolymer of these resins.

Novolac Resin (F1)

Resins represented by the formula (b1) may be used as the novolac resin (F1).

[Chem. 1]

(b1)

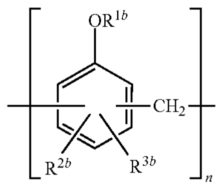

In the formula (b1), $R^{1b}$ represents an acid-dissociable, dissolution inhibiting group, $R^{2b}$ and $R^{3b}$ each independently represent a hydrogen atom or a C1-C6 alkyl group, and n represents the number of a repeating unit consisting of a structure in the brackets.

The acid dissociable, dissolution inhibiting group represented by $R^{1b}$ is preferably a C1-C6 linear alkyl group, a C3-C6 branched alkyl group, a C3-C6 cyclic alkyl group, a tetrahydropyranyl group, a tetrahydrofuranyl group, or a trialkylsilyl group.

Specific examples of the acid dissociable, dissolution inhibiting group represented by $R^{1b}$ include methoxyethyl, ethoxyethyl, n-propoxyethyl, isopropoxyethyl, n-butoxyethyl, isobutoxyethyl, tert-butoxyethyl, cyclohexyloxyethyl, methoxypropyl, ethoxypropyl, 1-methoxy-1-methylethyl, 1-ethoxy-1-methylethyl, tert-butoxycarbonyl, tert-butoxycarbonylmethyl, trimethylsilyl, and tri-tert-butyldimethylsilyl groups.

Polyhydroxystyrene Resin (F2)

Resins represented by the following formula (b4) may be used as the polyhydroxystyrene resin (F2).

[Chem. 2]

(b4)

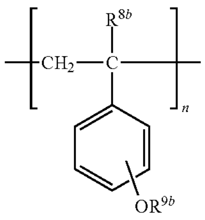

In the formula (b4), $R^{8b}$ represents a hydrogen atom or a C1-C6 alkyl group, $R^{9b}$ represents an acid-dissociable, dissolution inhibiting group, and n represents the number of a repeating unit consisting of a structure in the brackets.

The C1-C6 alkyl group is a C1-C6 linear alkyl group, a C3-C6 branched alkyl group, or a C3-C6 cyclic alkyl, group. Examples thereof include methyl, ethyl, propyl, isopropyl, n-butyl, isobutyl, tert-butyl, pentyl, isopentyl, and neopentyl groups. Examples of the cyclic alkyl group include cyclopentyl and cyclohexyl groups.

Examples of the acid-dissociable, dissolution inhibiting group represented by include the acid dissociable, dissolution inhibiting groups listed as examples for $R^{1b}$.

The polyhydroxystyrene resin (F2) may optionally contain other polymerizable compounds as structural units to appropriately control the physical and chemical properties. The polymerizable compounds may be known radically polymerizable compounds or anionically polymerizable compounds. Examples thereof include: monocarboxylic acids, such as acrylic acid; dicarboxylic acids, such as maleic acid, fumaric acid, and itaconic acid; methacrylic acid derivatives having a carboxyl group and an ester bond, such as 2-methacryloylcxyethyl succinic acid; (meth)acrylic acid alkyl esters, such as methyl (meth)acrylate; (meth) acrylic acid hydroxyalkyl esters, such as 2-hydroxyethyl (meth)acrylate; dicarboxylic acid diesters, such as diethyl maleate; vinyl group-containing aromatic compounds, such as styrene and vinyl toluene; vinyl group-containing aliphatic compounds, such as vinyl acetate; conjugated diolefins, such as butadiene and isoprene; nitrile group-containing polymerizable compounds, such as acrylonitrile; chlorine-containing polymerizable compounds, such as vinyl chloride; and amide bond-containing polymerizable compounds, such as acrylamide.

Acrylic Resin (F3)

Resins represented by the following formulas (b5) to (b10) may be used as the acrylic resin (F3).

[Chem. 3]

(b5)

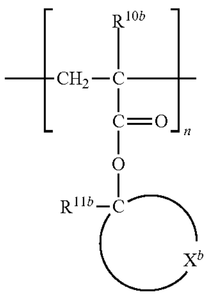

-continued (b6)

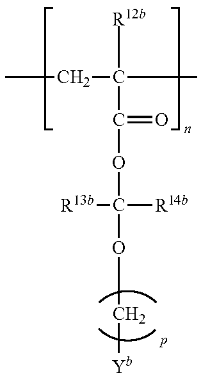

(b7)

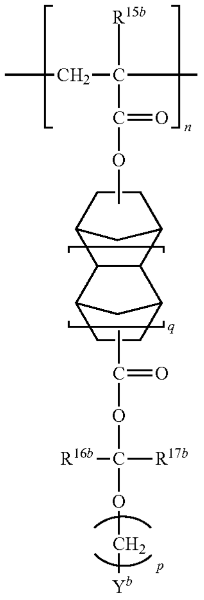

[Chem. 4]

(b8)

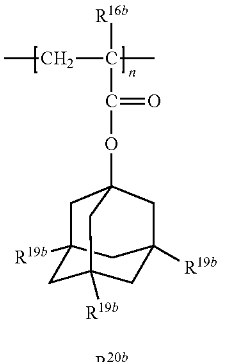

(b9)

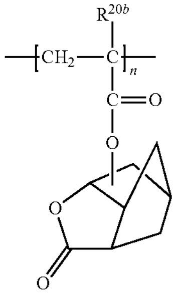

-continued (b10)

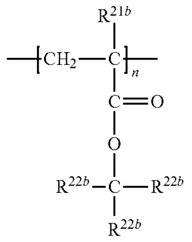

In the formulas (b5) to (b7), $R^{10b}$ to $R^{17b}$ each independently represent a hydrogen atom, a C1-C6 linear alkyl group, a C3-C6 branched alkyl group, a fluorine atom, a fluorinated C1-C6 linear alkyl group, or a fluorinated C3-C6 branched alkyl group; $X^b$, together with a carbon atom to which it is bound, forms a C5-C20 hydrocarbon ring; $Y^b$ represents an optionally substituted aliphatic ring group or an alkyl group; n represents the number of a repeating unit consisting of a structure in the brackets; p represents an integer of 0 to 4; and q represents 0 or 1.

In the formula (b8), the formula (b9), and the formula (b10), $R^{18b}$, $R^{20b}$, and $R^{21b}$ each independently represent a hydrogen atom or a methyl group. In the formula (b8), $R^{19b}$s each independently represent a hydrogen atom, a hydroxyl group, a cyano group, or a $COOR^{23b}$ group ($R^{23b}$ to represents a hydrogen atom, a C1-C4 linear alkyl group, a C3-C4 branched alkyl group, or a C3-C20 cycloalkyl group) In the formula (b10), $R^{23b}$s each independently represent a C4-C20 monovalent alicyclic hydrocarbon group or a derivative thereof, a C1-C4 linear alkyl group, or a C3-C4 branched alkyl group. At least one $R^{22b}$ is the alicyclic hydrocarbon group or a derivative thereof, or alternatively two of $R^{22b}$s bound to each other, together with a carbon atom to which both of them are bound, form a C4-C20 divalent alicyclic hydrocarbon group or a derivative thereof. The remaining $R^{22b}$ (s) each represent a C1-C4 linear alkyl group, a C3-C4 branched alkyl group, or a C4-C20 monovalent alicyclic hydrocarbon group or a derivative thereof.

The acrylic resin (F3) is preferably used as the component (F).

The component (F) has a polystyrene-equivalent weight average molecular weight of preferably 10,000 to 600,000, more preferably 50,000 to 600,000, still more preferably 230,000 to 550,000. When the component (F) has the above-mentioned weight average molecular weight, a resist with excellent resin physical properties may be obtained.

Moreover, the component (F) is preferably a resin having a dispersibility of 1.05 or higher. Herein, the term "dispersibility" is a quotient of the weight average molecular weight divided by the number average molecular weight. When the component (F) has the above-mentioned dispersibility, a resist with excellent plating resistance and excellent resin physical properties may be obtained.

The amount of the component (F) in the solids of the chemically amplifiable positive photoresist composition is preferably from 5 to 60% by weight.

Alkali Soluble Resin (G)

The chemically amplifiable positive photoresist composition of the present invention preferably further contains an alkali soluble resin (hereinafter, referred to as "component (G)") to improve the resin physical properties of a resist. The component (G) is preferably at least one selected from the group consisting of a novolac resin, a polyhydroxystyrene resin, an acrylic resin, and a polyvinyl resin.

The amount of the component (G) per 100 parts by weight of the component (F) is preferably from 5 to 95 parts by weight, more preferably from 10 to 90 parts by weight. When the amount is 5 parts by weight or more, the resin physical properties of a resist can be improved. When the amount is 95 parts by weight or less, film loss during development tends to be prevented.

Acid Diffusion Control Agent (H)

The chemically amplifiable positive photoresist composition of the present invention preferably further contains an acid diffusion control agent (H) (hereinafter, referred to as "component (H)") to improve resist pattern shapes, post-exposure delay stability, and the like. The component (H) is preferably a nitrogen-containing compound. The component (H) may optionally contain an organic carboxylic acid or a phosphorous oxo acid, or a derivative thereof.

The chemically amplifiable positive photoresist composition of the present invention may further contain an adhesion aid to enhance the adhesion with a substrate. The adhesion aid is preferably a functional silane coupling agent.

The chemically amplifiable positive photoresist composition of the present invention may further contain a surfactant to improve coatability, defoaming properties, leveling properties, and the like.

The chemically amplifiable positive photoresist composition of the present invention may further contain an acid, an acid anhydride, or a high boiling point solvent for fine adjustment of the solubility in an alkaline developer.

The chemically amplifiable positive photoresist composition of the present invention basically does not need a sensitizer. If necessary, it may contain a sensitizer to supply sensitivity. The sensitizer may be a conventionally known one, and specific examples thereof include those mentioned above.

The amount of the sensitizer relative to total 100 parts by weight of the onium salt represented by the formula (1) is from 5 to 500 parts by weight, preferably from 10 to 300 parts by weight.

An organic solvent may be appropriately added to the chemically amplifiable positive photoresist composition of the present invention to control the viscosity. Specific examples of the organic solvent include those described above.

The amount of the organic solvent is preferably adjusted to a solid concentration of 30% by weight or higher so that a photoresist layer formed with the chemically amplifiable positive photoresist composition (for example, by spin coating) has a thickness of 5 μm or more.

The chemically amplifiable positive photoresist composition for thick film may be prepared simply by mixing and stirring the components by a usual method, for example. If necessary, a dispersing device such as a dissolver, a homogenizer, or a three-roll mill may be used for dispersion or mixing. The obtained mixture may be filtrated with a mesh or a membrane filter.

The chemically amplifiable positive photoresist composition of the present invention is suitable for forming a photoresist layer having a thickness of usually 5 to 150 μm, more preferably 10 to 120 μm, still more preferably 10 to 100 μm on a support. The resulting photoresist laminate includes a support and a photoresist layer including the chemically amplifiable positive photoresist composition of the present invention stacked on the support.

Any support may be used, including conventionally known ones, examples thereof include substrates for electronic components and those substrates having prescribed wiring patterns. The substrate may be, for example, a metal substrate from silicon, silicon nitride, titanium, tantalum, palladium, titanium tungsten, copper, chromium, iron, aluminum, or the like or a glass substrate. The chemically amplifiable positive photoresist composition of the present invention can form & resist pattern favorably on a copper substrate. Examples of the material of the wiring pattern include copper, solder, chromium, aluminum, nickel, and gold.

For example, the photoresist laminate may be produced as follows: A solution of the chemically amplifiable positive photoresist composition prepared as described above is applied to a support, and then the solvent is evaporated by heating, thereby forming a desired film. Examples of the method for applying the solution to the support include spin coating, slit coating, roll coating, screen printing, and applicator coating. The film of the composition of the present invention may be pre-baked usually at a temperature of from 70° C. to 150° C., preferably from 80° C. to 140° C. for about 2 to 60 minutes. The conditions vary depending on the types and blending ratio of the components in the composition, the thickness of the film, and the like.

The photoresist layer has a thickness of usually from 5 to 150 μm, preferably from 10 to 120 μm, more preferably from 10 to 100 μm.

To form a resist pattern using a resulting photoresist laminate, the photoresist layer is portion-selectively irradiated with (exposed to) light or radiation, such as ultraviolet light or visible light having a wavelength of from 300 to 500 nm through a prescribed pattern mask.

Herein, the term "light" refers to any light that can activate the photoacid generator to generate an acid and encompasses ultraviolet light, visible light, and far ultraviolet light. The term "radiation" refers to X-rays, electron beam, ion beam, or the like. Examples of the source of the light or radiation include low-pressure mercury lamps, high-pressure mercury lamps, ultra-high pressure mercury lamps, metal halide lamps, argon gas lasers, and LED lamps. For example, the dose of radiation exposure varies depending on the types and amounts of the components in the composition, the thickness of the film, and the like. For example, the dose using an ultra-high pressure mercury lamp is from 50 to 10,000 $mJ/cm^2$.

After exposure, the photoresist laminate is heated by a known method to promote acid diffusion, thereby changing the alkali solubility of the exposed part of the photoresist layer. Subsequently, unnecessary parts are dissolved and eliminated using a developer, for example, a prescribed alkali aqueous solution. Thus, a prescribed resist pattern is obtained.

The development time is usually 1 to 30 minutes. The time varies depending on the types and blending ratio of the components in the composition and the dry thickness of the composition film. The development may be performed by any technique, such as liquid filling, dipping, puddling, or spraying. After development, washing with running water is performed for 30 to 90 seconds, followed by drying using an air gun, an oven, or the like.

A conductor such as metal may be embedded to the resist-free parts (parts where the resist is removed by the alkaline developer) of the resist pattern by, for example, plating, whereby connecting terminals such as metal posts or bumps can be formed. Plating can be performed by any method, including conventionally known methods. Preferred examples of the plating liquid include solder plating, copper plating, gold plating, and nickel plating liquids. Lastly, the remaining resist pattern is removed with a stripping solution by a conventional method.

The chemically amplifiable positive photoresist, composition of the present invention can be used in the form of a dry film. The dry film includes a layer of the chemically amplifiable positive photoresist, composition of the present invention and protective films formed on the respective faces of the layer. The layer of the chemically amplifiable positive photoresist composition has a thickness of usually from 10 to 150 μm, preferably from 20 to 120 μm, more preferably from 20 to 80 μm. Any protective film may be used, such as a resin film conventionally used for dry films. In an exemplary embodiment, a polyethylene terephthalate film is present on one face and a film, selected from the group consisting of a polyethylene terephthalate film, a polypropylene film, and a polyethylene film is present on the other face.

For example, the chemically amplifiable positive dry film can be produced as follows: A solution of the chemically amplifiable positive photoresist composition prepared as described above is applied to one of the protective films, and then the solvent is evaporated by heating, thereby forming a desired film. Drying is performed usually at 60° C. to 100° C. for about 5 to 20 minutes. The drying conditions vary depending on the types and blending ratio of the components in the composition, the thickness of the film, and the like.

A resist pattern may be formed using the chemically amplifiable dry film as follows: One of the protective films on the chemically amplifiable positive dry film is peeled, and then the dry film is stacked on a support, with the peeled-side face facing the support, thereby preparing a photoresist layer. Next, the resist is dried by prebaking, and then the other protective film is peeled.

The thus obtained photoresist layer on the support can be processed into a resist pattern as described for the photoresist layer formed by direct application to a support.

Regarding the chemically amplifiable negative photoresist composition (3), the onium salt (A) of the present invention which is a compound generating an acid when exposed to light or radiation serves as an acid generator, and an alkali soluble resin (I) having a phenolic hydroxy group reacts with a crosslinking agent (J) under the action of the acid generated from the onium salt (A).

Alkali Soluble Resin (I) Having a Phenolic Hydroxy Group

Examples of the "alkali soluble resin having a phenolic hydroxy group" in the present invention (hereinafter, referred to as "phenolic resin (I)") include novolac resin, polyhydroxystyrene, polyhydroxystyrene copolymers, copolymers of hydroxystyrene and styrene, copolymers of hydroxystyrene, styrene, and a (meth)acrylic acid derivative, phenol-xylylene glycol condensation resin, cresol-xylylene glycol condensation resin, and phenol-dicyclopentadiene condensation resin. Preferred among these are novolac resin, polyhydroxystyrene, polyhydroxystyrene copolymers, copolymers of hydroxystyrene and styrene, copolymers of hydroxystyrene, styrene, and a (meth)acrylic acid derivative, and phenol-xylylene glycol condensation resin. The phenolic resin (I) may be used alone or in the admixture of two or more.

The phenolic resin (I) may contain a low molecular weight phenolic compound as one of the components thereof.

Examples of the low molecular weight phenolic compound include 4,4'-dihydroxydiphenylmethane and 4,4'-dihydroxydiphenyl ether.

Crosslinking Agent (J)

The "crosslinking agent" in the present invention (hereinafter/also referred to as "crosslinking agent (J)") may be any crosslinking agent functioning as a crosslinkable component (curing component) that reacts with the phenolic resin (I). Examples of the crosslinking agent (J) include compounds having at least two alkyl-etherified amino groups per molecule, compounds having at least two alky-etherified benzene skeletons per molecule, oxirane ring-containing compounds, thiirane ring-containing compounds, oxetanyl group-containing compounds, and isocyanate group-containing compounds (including blocks thereof).

Of these, the crosslinking agent (J) is preferably a compound having at least two alkyl-etherified amino groups per molecule or an oxirane ring-containing compound. It is more preferably a combination of a compound having at least two alkyl-etherified amino groups per molecule and an oxirane ring-containing compound.

The amount of the crosslinking agent (J) in the present invention per 100 parts by weight of the phenolic resin (I) is preferably from 1 to 100 parts by weight, more preferably from 5 to 50 parts by weight. When the amount or the crosslinking agent (J) is from 1 to 100 parts by weight, preferably, a curing reaction can sufficiently proceed, and a resulting cured product has high resolution, good pattern shape, excellent heat resistance, and excellent electrical insulation.

When a compound having alkyl-etherified amino groups and an oxirane ring-containing compound are used in combination, the oxirane ring-containing compound content in total 100% by weight of the compound having alkyl-etherified amino groups and the oxirane ring-containing compound is preferably 50% by weight or lower, more preferably 5 to 40% by weight/particularly preferably 5 to 30% by weight.

The above content is preferred because the resulting cured film can have excellent chemical resistance without losing high resolution properties.

Crosslinked Fine Particles (K)

The chemically amplifiable negative photoresist composition of the present invention may further contain crosslinked fine particles (hereinafter, also referred to as "crosslinked fine particles (K)") to enhance the durability or heat impact resistance of resulting cured products.

The crosslinked fine particles (K) have an average particle size of usually 30 to 500 nm, preferably 40 to 200 nm, still more preferably 50 to 120 nm.

The particle size of the crosslinked fine particles (K) may be controlled by any method. For example, when the crosslinked fine particles are synthesized by emulsion polymerization, the particle size can be controlled by changing the amount of an emulsifier to control the number of micelles during the emulsion polymerization.

The average particle size of the crosslinked fine particles (K) is a value measured with a light scattering flow distribution measuring device or the like using a dispersion of the crosslinked fine particles diluted by a usual method.

The amount of the crosslinked fine particles (K) per 100 parts by weight of the phenolic resin (I) is preferably from 0.5 to 50 parts by weight, more preferably from 1 to 30 parts by weight. When the amount of the crosslinked fine particles (K) is from 0.5 to 50 parts by weight, excellent compatibility with other components or excellent dispersion is obtained, and the heat impact resistance and heat resistance of a resulting cured film can be improved.

Adhesion Aid

The chemically amplifiable negative photoresist composition of the present invention may contain an adhesion aid to enhance adhesion to a substrate.

Examples of the adhesion aid include functional silane coupling agents having reactive substituents such as carboxyl groups, methacryloyl groups, isocyanate groups, and epoxy groups.

The amount of the adhesion aid per 100 parts by weight, of the phenolic resin (I) is preferably from 0.2 to 10 parts by weight, more preferably from 0.5 to 8 parts by weight. When the amount of the adhesion aid is from 0.2 to 10 parts by weight, advantageously, not only excellent storage stability but also good adhesion can be obtained.

Solvent

The chemically amplifiable negative photoresist composition of the present invention may contain a solvent to improve the handleability of the resin composition or to control the viscosity or storage stability.

Any solvent may be used, and specific examples thereof include those mentioned above.

The chemically amplifiable negative photoresist composition of the present invention may contain a sensitizer, if necessary. Examples of the sensitizer include conventionally known ones, and specific examples thereof include those mentioned above.

The amount of the sensitizer relative to total 100 parts by weight of the sulfonium salt represented by the formula (1) is from 5 to 500 parts by weight, preferably from 10 to 300 parts by weight.

Other Additives

The chemically amplifiable negative photoresist composition of the present invention may contain other additives, if necessary, as long as the features of the present invention are not impaired. Examples of other additives include inorganic filler, quenchers, leveling agents, and surfactants.

The chemically amplifiable negative photoresist composition of the present invention may be prepared by any method including known methods. It may be prepared by stirring a completely sealed sample vessel containing the components on a wave rotor.

The cured product of the present invention is obtainable by curing the chemically amplifiable negative photoresist composition.

The chemically amplifiable negative photoresist composition of the present invention has a high film-remaining ratio and excellent resolution properties. A cured product thereof has excellent electrical insulation, excellent heat impact resistance, and the like. Thus, the cured product is preferably used as a surface protective film, a planarizing film, an interlayer insulating film material, or the like of electronic components such as semiconductor devices and semiconductor packages.

The cured product of the present invention is produced as follows: First, the chemically amplifiable negative photoresist composition of the present invention is applied to a support (e.g., resin-coated copper foil, copper clad laminate, or silicon wafer or alumina substrate having a sputtered metal film) and then dried to evaporate a solvent, thereby forming a film. Then, the film is exposed to light through a desired pattern mask.

Subsequently, the film is heated (hereinafter, this heat treatment is referred to as "PEB") to promote the reaction between the phenolic resin (F) and the crosslinking agent (G). Next, development is performed using an alkaline developer, and unexposed parts are dissolved and removed, thereby forming a desired pattern. Thereafter, heat treatment is performed for the expression of insulating film properties. Thus, a cured film is obtained.

Examples of the method to apply the resin composition to the support include dipping, spraying, bar coating, roll coating, and spin coating. The film thickness may be appropriately controlled by changing the application technique or changing the solid concentration or viscosity of composition solutions.

Examples of the radiation for the exposure include ultraviolet light, electron beam, and laser beam applied by low-pressure mercury lamps, high-pressure mercury lamps, metal halide lamps, g-ray steppers, h-ray steppers, i-ray steppers, gh-ray steppers, and ghi-ray steppers. The exposure dose is appropriately selected depending on the light source to be used, the resin film thickness, or the like. For example, when the exposure is performed by ultraviolet light irradiation from a high-pressure mercury lamp, the dose for a resin film having a thickness of 1 to 50 μm is about 100 to 50,000 $J/m^2$.

After exposure, the PEB treatment is performed to promote the curing reaction by the action of a generated acid between the phenolic resin (F) and the crosslinking agent (G). The PEB conditions vary depending on the amount of the resin composition, film thickness, or the like. The PEB treatment is performed usually at 70° C. to 150° C., preferably 80° C. to 120° C. for about 1 to 60 minutes. Next, development is performed using an alkaline developer, and unexposed parts are dissolved and removed, thereby forming a desired pattern. Examples of the method of development include shower development, spray development, immersion development, and puddle development. The development is performed usually at 20° C. to 40° C. for about 1 to 10 minutes.

The film after development is sufficiently cured by heating to fully express the properties as an insulating film. The curing conditions are not limited and are set depending on the intended use of a cured product. The composition may be cured by heating at a temperature of 50° C. to 250° C. for about 30 minutes to 10 hours. The heating may include two stages for sufficient curing or prevention of the deformation of resulting pattern shapes. For example, the composition may be cured by heating at a temperature of 50° C. to 120° C. for about five minutes to two hours at the first stage, and then at a temperature of 80° C. to 250° C. for about 10 minutes to 10 hours. A heating device such as a usual even or an infrared heating furnace may be used under the above-mentioned curing conditions.

EXAMPLES

The present invention will be specifically described with reference to examples and comparative examples, but the present invention is not limited thereto. The term "part(s)" in those examples mean "part(s) by weight".

Production Examples of Anions (B1) to (B6) and (B'1)

Production Example of Anion (B1)

With cooling, 4.44 g of potassium fluoride (KF) was slowly added to 50.0 g of dimethoxyethane. Thereafter, 32.5 g of tris(pentafluoroethyl)difluorophosphorane was added thereto with stirring. It was slowly added under cooling so that the temperature of the reaction mixture was controlled to 30° C. or lower, followed by reaction. Thus, a solution of a potassium salt of tris(heptafluoroethyl)trifluorophosphonate ($K^+[(C_2F_3)_3(F)_3P]^-$) was obtained. F-NMR results show that the proportion of the facial isomer in a total of the two isomers was 0.0% by weight.

Production Example of Anion (B2)

With cooling, 4.44 g potassium fluoride (KF) was slowly added to 50.0 g of dimethoxyethane. Thereafter, 43.9 g of tris(pentafluoropropyl)difluorophosphorane was added thereto with stirring. It was slowly added under cooling so that the temperature of the reaction mixture was controlled to 30° C. or lower, followed by reaction. Thus, a solution of a potassium salt of tris(heptafluoropropyl)trifluorophosphonate ($K^+[(C_3F_7)_5(F)_5P]^-$) was obtained. F-NMR results show that the proportion of the facial isomer in a total of the two isomers was 0.0% by weight.

Production Example of Anion (B3)

First, 7.04 g of a 40% aqueous hydrofluoric acid solution was diluted with 19.0 g of ion exchange water. To the dilution cooled to 5° C. or lower in advance was slowly added 60.0 g of tris(pentafluoroethyl)difluorophosphorane with stirring. It was slowly added under cooling so that the temperature of the reaction mixture was controlled to 10° C. or lower, followed by reaction. Thereafter, a solution prepared by dissolving 7.90 g of potassium hydroxide in 30 g of ion exchange water was added thereto. Thus, a solution of a potassium salt of tris(heptafluoropropyl)trifluorophosphonate ($K^+[(C_2F_5)_3(F)_3P]^-$) was obtained. F-NMR results show that the proportion of the facial isomer in a total of the two isomers was 0.1% by weight.

Production Example of Anion (B4)

First, 5.65 g of a 40% aqueous hydrofluoric acid solution was diluted with 6.73 g of ion exchange water. To the dilution cooled to 5° C. or lower in advance was slowly added 47.8 g of tris(pentafluoroethyl)difluorophosphorane with stirring. It was slowly added under cooling so that the temperature of the reaction mixture was controlled to 10° C. or lower, followed by reaction. Thereafter, a solution prepared by dissolving 6.29 g of potassium hydroxide in 30 g of ion exchange water was added thereto. Thus, a solution of a potassium salt of tris(heptafluoropropyl)trifluorophosphonate ($K^+[(C_2F_5)_3(F)_3P]^-$) was obtained. F-NMR results show that the proportion of the facial isomer in a total of the two isomers was 5.0% by weight.

Production Example of Anion (B5)

With cooling, 1.66 g of hydrogen fluoride (HF) was slowly added to 11.0 g of diethyl ether. Thereafter, 33.6 g of tris(pentafluoroethyl)difluorophosphorane was slowly added thereto with stirring. It was slowly added under cooling so that the temperature of the reaction mixture was controlled to 5° C. or lower, followed by reaction. Thereafter, 4.42 g of potassium hydroxide was added thereto. Thus, a solution of a potassium salt of tris(heptafluoropropyl)trifluorophosphonate ($K^+[(C_2F_5)_3(F)_3P]^-$) was obtained. F-NMR results show that the proportion of the facial isomer in a total of the two isomers was 14.6% by weight.

Production Example of Anion (B6)

First, 7.51 g of a 40% aqueous hydrofluoric acid solution was diluted with 10.0 g of ion exchange water. To the dilution cooled to 5° C. or lower in advance was slowly added 63.6 g of tris(pentafluorophenyl)difluorophosphorane with stirring. It was slowly added under cooling so that the temperature of the reaction mixture was controlled to 10° C. or lower, followed by reaction. Thereafter, a solution prepared in advance by dissolving 8.36 g of potassium hydroxide in 30 g of ion exchange water was added thereto. Thus, a solution of a potassium salt of tris(pentafluorophenyl) trifluorophosphonate ($K^+[(C_2F_5)_3(F)_3P]^-$) was obtained. F-NMR results show chat the proportion of the facial isomer in a total of the two isomers was 5.0% by weight.

Production Example of Anion (B'1)

With cooling, 1.64 g of hydrogen fluoride (HF) was slowly added to 6.00 g of methanol. Thereafter, 32.5 g of tris(pentafluoroethyl)difluorophosphorane was slowly added thereto with stirring. It was slowly added under cooling so that the temperature of the reaction mixture was controlled to 5° C. or lower, followed by reaction. Thereafter, 4.28 g of potassium hydroxide was added thereto. Thus, a solution of a potassium salt of tris(heptafluoropropyl)trifluorophosphonate ($K^+[(C_2F_5)_3(F)_3P]^-$) was obtained. F-NMR results show that the proportion of the facial isomer in a total of the two isomers was 18.4% by weight.

Example of Onium Salt (A1-1)

Production of 4-(phenylthio)phenyldiphenylsulfonium-tris(pentafluoroethyl)trifluorophosphonate (Facial Isomer of Anion: 0.0% by Weight)

First, 12.12 g of diphenyl sulfoxide, 9.3 g of diphenyl sulfide, and 43.0 g of methanesulfonic acid were uniformly mixed, followed by dropwise addition of 7.9 g of acetic anhydride. The mixture was reacted at 50° C. for five hours, followed by cooling to room temperature. To the reaction solution was added dropwise 124.5 g of a 20% aqueous anion (B1) solution prepared by solvent substitution of the anion (B1) solution, and these were stirred for two hours. The precipitated oily substance was extracted into 120 g of ethyl acetate, the aqueous layer was removed, and the organic layer was further washed three times. The solvent was removed from the organic layer, 50 g of toluene was added for dissolution, and 270 g of hexane was added thereto, followed by mixing. The mixture was allowed to stand for one hour to separate into two layers. The upper layer was removed, and 150 g of hexane was added to the remaining lower layer. These are sufficiently stirred to precipitate crystals. The crystals were collected by filtration and dried under reduced pressure. Thus, 4-(phenylthio) phenyldiphenylsulfonium-tris(pentafluoroethyl)trifiuorophosphonate (A1-1) (facial isomer of anion: 0.0% by weight) was obtained. The compound (A1-1) is represented by the following (a1).

[Chem. 5]

(a1)

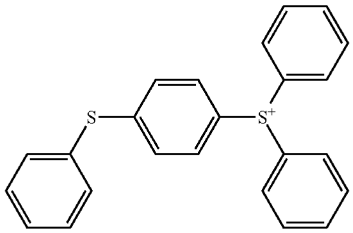

$[(C_2F_5)_3(F)_3P]^-$

Examples of Onium Salts (A1-2) to (A1-6) and Comparative Example of Onium Salt (A'1-1)

Onium salts (A1-2) to (A1-6) and (A'1-1) were obtained as in the production example of (A1-1) except that anions (B2) to (B6) and (B'1) was used instead of anion (B1). Only in the case of anion (B2), the amount of the 20% aqueous anion (B2) solution was changed to 167 g. The following describes the names of the synthesized compounds.

(A1-2): 4-(Phenylthio)phenyldiphenylsulfonium-tris (heptafluoropropyl)trifluorophosphonate (facial isomer of anion: 0.0% by weight)

(A1-3): 4-(Phenylthio)phenyldiphenylsulfonium-tris (pentafluoroethyl)trifluorophosphonate (facial isomer of anion: 0.1% by weight)

(A1-4): 4-(Phenylthio)phenyldiphenylsulfonium-tris (pentafluoroethyl)trifluorophosphonate (facial isomer of anion: 5.0% by weight)

(A1-5): 4-(Phenylthio)phenyldiphenylsulfonium-tris (pentafiuoroethyl)trifluorophosphonate (facial isomer of anion: 14.6% by weight)

(A1-6): 4-(Phenylthio)phenyidiphenyisulfonium-tris (pentafluorophenyl)trifluorophosphonate (facial isomer of anion: 5.0% by weight)

(A'1-1): 4-(Phenylthio)phenyldiphenylsulfonium-tris (pentafluoroethyl)trifluorophosphonate (facial isomer of anion: 18.4% by weight)

The compound (A1-2) is represented by the chemical formula (a2), the compounds (A1-3) to (A1-5) and (A'1-1) are each represented by the chemical formula (a1), and the compound (A1-6) is represented by the chemical formula (a3).

[Chem. 6]

(a2)

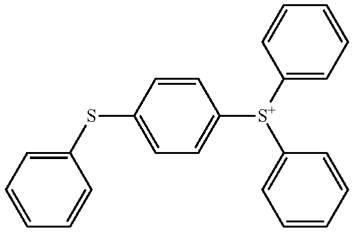

$[(C_3F_7)_3(F)_3P]^-$

-continued

[Chem. 7]

(a3)

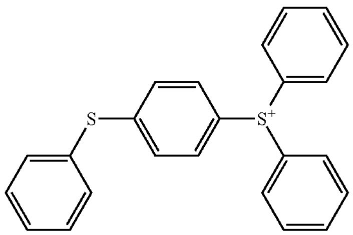

$[(C_6F_5)_3(F)_3P]^-$

Example of Onium Salt (A2-1)

Production of (4-isopropylphenyl)tolyliodonium-tris (pentafluoroethyl)trifluorophosphonate (Facial Isomer of Anion: 0.0% by Weight)

To 20 g of 4-methyliodobenzene were added 50 g of acetic acid and 10 g of sulfuric acid for dissolution, and 10 g of potassium persulfate was added little by little at 15° C. or lower with cooling in an ice bath. The reaction was carried out at 20° C. for four hours, to which 24.4 g of cumene was added dropwise while the temperature was kept not to exceed 20° C. Thereafter, the contents were reacted at room temperature for 20 hours. The reaction solution was added to 50 parts of an aqueous solution containing the same molar amount of anion (B1) as that of the obtained iodonium salt, followed by stirring for three hours. To the solution was added 500 parts of dichloromethane. The solution was allowed to stand and subjected to liquid-liquid-separation to remove the aqueous layer. The organic layer was washed with 100 parts of water five times. The dichloromethane was concentrated, and recrystallization with cyclohexane was performed to give (4-isopropylphenyl)tolyliodonium-tris (pentafluoroethyl)trifluorophosphonate (facial isomer of anion: 0.0% by weight). The resulting compound is represented by the following (a4).

[Chem. 8]

(a4)

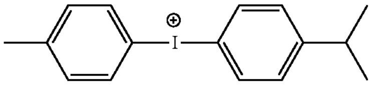

$[(C_2F_5)_3(F)_3P]^-$

Examples of Onium Salts (A2-2) to (A2-6) and Comparative Example of Onium Salt (A'2-1)

Onium salts (A2-2) to (A2-6) and (A'2-1) were obtained as in the production example of (A2-1) except that anions (B2) to (B6) and anion (B'1) were used instead of anion (B1). Only in the case of anion (B2), the amount of the 20% aqueous anion (B2) solution was changed to 167 g. The following describes the names of the synthesized compounds.

(A2-2): (4-Isopropylphenyl)tolyliodonium-tris(heptafluoropropyl)trifiuorophosphonate (facial isomer of anion: 0.0% by weight)

(A2-3): (4-Isopropylphenyl)tolyliodonium-tris(pentafluoroethyl)trifluorophosphonate (facial isomer of anion: 0.1% by weight)

(A2-4): (4-Isopropylphenyl)tolyliodonium-tris(pentafluoroethyl)trifluorophosphonate (facial isomer of anion: 5.0% by weight)

(A2-5): (4-Isopropylphenyl)tolyliodonium-tris(pentafluoroethyl)trifluorophosphonate (facial isomer of anion: 14.6% by weight)

(A2-6): (4-Isopropylphenyl)tolyliodonium-tris(pentafluorophenyl)trifluorophosphonate (facial isomer of anion: 5.0% by weight)

(A'2-1): (4-Isopropylphenyl)tolyliodonium-tris(pentafluoroethyl)trifluorophosphonate (facial Isomer of anion: 18.4% by weight)

The compound (A2-2) is represented by the chemical formula (a5), the compounds (A2-3) to (A2-S) and (A'2-1) are each represented by the chemical formula (a4), and the compound (A2-6) is represented by the chemical formula (a6).

[Chem. 9]

(a5)

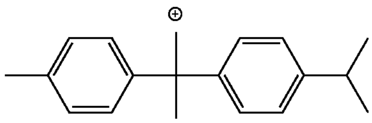

$[(C_3F_7)_3(F)_3P]^-$

[Chem. 10]

(a6)

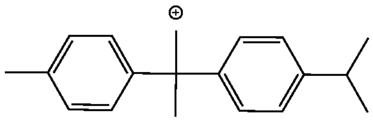

$[(C_6F_5)_3(F)_3P]^-$

Example of Onium Salt (A3-1)

Production of [4-(4-biphenylthio)phenyl]-4-biphenylphenylsulfonium-tris(pentafluoroethyl)trifluorophosphonate (Facial Isomer of Anion: 0.0% by Weight)

First, 11 g of 4-[(phenyl)sulfinyl]biphenyl, 12 g of 4-(phenylthio)biphenyl, 22 g of acetic anhydride, and 16 parts of methanesulfonic acid were homogeneously mixed and reacted at 65° C. for three hours. The reaction solution was cooled to room temperature, poured into 100 mL of ion exchange water, and subjected to extraction with 100 g of dichloromethane. The aqueous layer was washed with water until the pH reached neutral. The dichloromethane layer was transferred into a rotary evaporator, and the solvent was evaporated. Thus, a brown solid was obtained. The brown solid was washed with ethyl acetate/hexane and the organic solvent was concentrated to give an intermediate.

Next, 6.2 g of the intermediate was dissolved in 60 mL of dichloromethane and combined with 70 g of an aqueous solution containing anion (B1) at room temperature, and the mixture was stirred as it was for three hours. The dichloromethane layer was washed with water by liquid-liquid separation five times and transferred into a rotary evaporator, and the solvent was evaporated. Thus, [4-(4-biphenylthio)phenyl]-4-biphenylphenylsulfonium-tris(pentafluoroethyl)trifluorophosphonate (facial isomer of anion: 5.0% by weight) was obtained. The compound is represented by the chemical formula (a7).

[Chem. 11]

(a7)

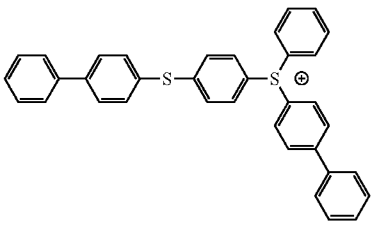

$[(C_2F_5)_3(F)_3P]^-$

Examples of Onium Salts (A3-2) to (A3-6) and Comparative Example of Onium Salt (A'3-1)

Onium salts (A3-2) to (A3-6) and (A'3-1) were obtained as in the production example of (A3-1) except that anions (B2) to (B6) and anion (B'1) were used instead of anion (B1). Only in the case of anion (B2), the amount of the 20% aqueous anion (B2) solution was changed to 167 g. The following describes the names of the synthesized compounds.

(A3-2): [4-(4-Biphenylthio)phenyl]-4-biphenylphenylsulfonium-tris(heptafluoropropyl)trifluorophosphonate (facial isomer of anion: 0.0% by weight)

(A3-3): [4-(4-Biphenylthio)phenyl]-4-biphenylphenylsulfonium-tris(pentafluoroethyl)trifluorophosphonate (facial isomer of anion: 0.1% by weight)

(A3-4): [4-(4-Biphenylthio)phenyl]-4-biphenylphenylsulfonium-tris(pentafluoroethyl trifluorophosphonate (facial isomer of anion: 5.0% by weight)

(A3-5): [4-(4-Biphenylthio)phenyl]-4-biphenylphenylsulfonium-tris(pentafluoroethyl)trifluorophosphonate (facial isomer of anion: 14.6% by weight)

(A3-6): [4-(4-Biphenylthio)phenyl]-4-biphenylphenylsulfonium-tris(pentafluorophenyl)trifluorophosphonate (facial isomer of anion: 5.0% by weight) (A'3-1): [4-(4-Biphenylthio)phenyl]-4-biphenylphenylsulfonium-tris(pentafluoroethyl)trifluorophosphonate (facial isomer of anion: 18.4% by weight)

The compound (A3-2) is represented by the chemical formula (a8), the compounds (A3-3) to (A3-5) and (A'3-1) are each represented by the chemical formula (a7), and the compound (A3-6) is represented by the chemical formula (a9).

[Chem. 12]

(a8)

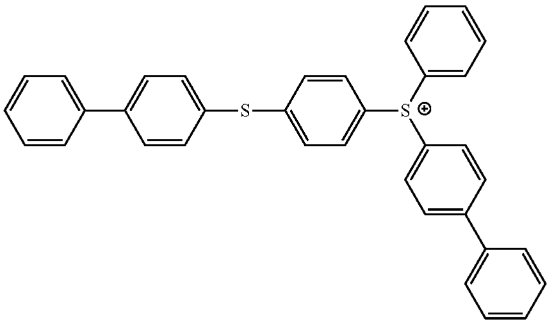

$[(C_3F_7)_3(F)_3P]^-$

-continued

[Chem. 13]

(a9)

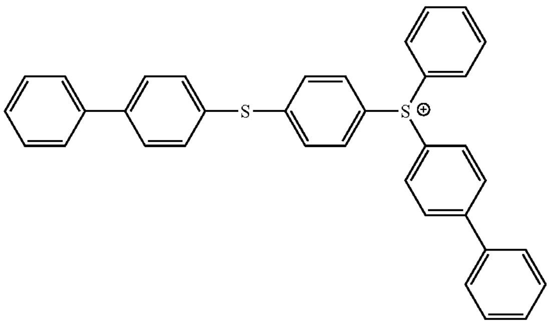

$[(C_6F_5)_3(F)_3P]^-$

Example of Onium Salt (A4-1)

Production of [4-(4-acetylphenylthio)]phenyldiphenylsulfonium-tris(pentafluoroethyl)trifluorophosphonate (Facial Isomer of Anion: 0.0% by Weight)

First, 89 parts of a dichloromethane solution containing 32 parts of (4-phenylthio)phenyldiphenylsulfonium trifluoromethanesulfonate was added dropwise to a suspension obtained by mixing 36 parts of aluminum chloride, 12 parts of acetyl chloride, and 200 parts of dichloromethane with stirring and cooling in the system at 10° C. or lower. After the dropwise addition, the mixture was stirred at room temperature for two hours, and 300 parts of cold water were added thereto. The upper layer was removed and the dichloromethane layer was washed with ion-exchanged water until the pH reached neutral. Next, 70 g of an aqueous solution containing anion (B1) was mixed therewith at room temperature, stirred as it was for three hours. The dichloromethane layer was washed with water by liquid-liquid separation five times and transferred into a rotary evaporator, and the solvent was evaporated. Thus, [4-(4-acetylphenylthio)]phenyldiphanylsulfonium-tris(pentafluoroethyl)trifluorophosphonate (facial isomer of anion: 0.0% by weight) was obtained. The compound is represented by the chemical formula (a10).

[Chem. 14]

(a10)

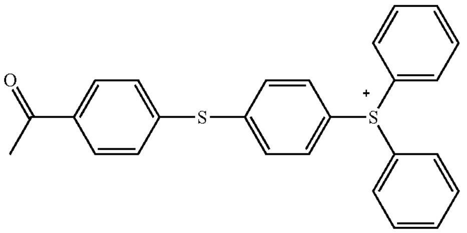

$[(C_2F_5)_3(F)_3P]^-$

Examples of Onium Salts (A4-2) to (A4-6) and Comparative Example of Onium Salt (A'4-1)

Onium salts (A4-2) to (A4-6) and (A'4-1) were obtained as in the production example of (A4-1) except that anions (B2) to (B6) and anion (B'1) were used instead of anion (B1). Only in the case of anion (B2), the amount of the 20% aqueous anion (B2) solution was changed to 167 g.

The following describes the names of the synthesized compounds.

(A4-2): [4-(4-Acetylphenylthio)]phenyldiphenylsulfonium-tris(heptafluoropropyl)trifluorophosphonate (facial isomer of anion: 0.0% by weight)

(A4-3): [4-(4-Acetylphenylthio)]phenyldiphenylsulfonium-tris(pentafluoroethyl)trifluorophosphonate (facial isomer of anion: 0.1% by weight)

(A4-4): [4-(4-Acetylphenylthio)]phenyldiphenylsulfonium-tris(pentafluoroethyl)trifluorophosphonate (facial isomer of anion: 5.0% by weight)

(A4-5): [4-(4-Acetylphenylthio)]phenyldiphenylsulfonium-tris(pentafluoroethyl)trifluorophosphonate (facial isomer of anion: 14.6% by weight)

(A4-6): [4-(4-Acetylphenylthio)]phenyldiphenylsulfonium-tris(pentafluorophenyl)trifluorophosphonate (facial isomer of anion: 5.0% by weight)

(A'4-1): [4-(4-Acetylphenylthio)]phenyldiphenylsulfonium-tris(pentafluoroethyl)trifluorophosphonate (facial isomer of anion: 18.4% by weight)

The compound (A4-2) is represented by the chemical formula (a11), the compounds (A4-3) to (A4-5) and (A'4-1) are each represented by the chemical formula (a10), and the compound (A4-6) is represented by the chemical formula (a12).

[Chem. 15]

(a11)

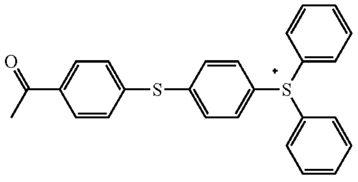

$[(C_3F_7)_3(F)_3P]^-$

[Chem. 15]

(a12)

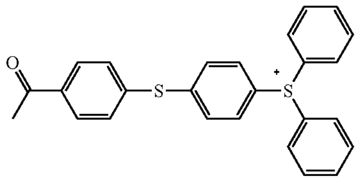

$[(C_3F_7)_3(F)_3P]^-$

Example of Onium Salt (A5-1)

Production of Fluorene-Based Sulfonium-Tris(pentafluoroethyl)trifluorophosphonate (Facial Isomer of Anion: 0.0% By Weight)

First, 1.0 parts of 2-[(phenyl) sulfinyl)]-9,9-dimethylfluorene, 1.1 parts of 2-(phenylthio)-9,9-dimethylfluorene, 2.0 parts of acetic anhydride, and 1.6 parts of methanesulfonic acid were charged and stirred at 65° C. for three hours. The reaction solution was cooled to room temperature, poured into 5.0 parts of ion exchange water, and subjected to extraction with 5.0 parts of dichloromethane. The aqueous layer was washed with ion exchange water until the pH reached neutral. Next, 70 g of an aqueous solution containing anion (B) was mixed with the dichloromethane layer with stirring at room temperature, stirred as it was for three hours. The dichloromethane layer was washed with water by liquid-liquid separation five times and transferred into a rotary evaporator, and the solvent was evaporated. Thus, [4-(4-acetylphenylthio)]phenyldiphenylsulfonium-tris(pentafluoroethyl)trifluorophosphonate (facial isomer of anion: 0.0% by weight) was obtained. The compound is represented by the chemical formula (a13).

[Chem. 17]

(a13)

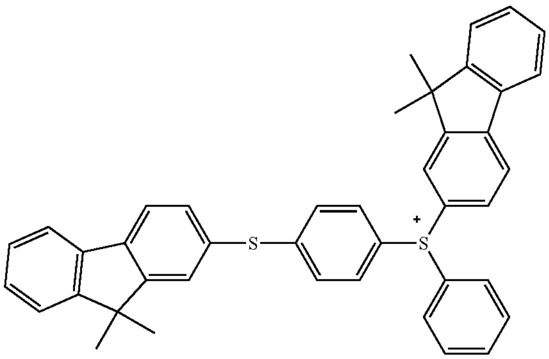

$[(C_2F_5)_3(F)_3P]^-$

Examples of Onium Salts (A5-2) to (A5-6) and Comparative Example of Onium Salt (A'5-1)

Onium salts (A5-2) to (A5-6) and (A'5-1) were obtained as in the production example of (A5-1) except that anions (B2) to (B6) and anion (B'1) were used instead of anion (B1). Only in the case of anion (B2), the amount of the 20% aqueous anion (B2) solution was changed to 167 g. The following describes the names of the synthesized compounds.

(A5-2): Fluorene-based sulfonium-tris(heptafluoropropyl)trifluorophosphonate (facial isomer of anion: 0.0% by weight)

(A5-3): Fluorene-based sulfonium-tris(pentafluoroethyl) trifluorophosphonate (facial isomer of anion: 0.1% by weight)

(A5-4): Fluorene-based sulfonium-tris(pentafluoroethyl) trifluorophosphonate (facial isomer of anion: 5.0% by weight)

(A5-5): Fluorene-based sulfonium-tris(pentafluoroethyl) trifluorophosphonate (facial isomer of anion: 14.6% by weight)

(A5-6): Fluorene-based sulfonium-tris(pentafluorophenyl)trifluorophosphonate (facial isomer of anion: 5.0% by weight)

(A'5-1): Fluorene-based sulfonium-tris(pentafluoroethyl) trifluorophosphonate (facial isomer of anion: 18.4% by weight)

The compound (A5-2) is represented by the chemical formula (a14), the compounds (A5-3) to (A5-5) and (A'5-1) are each represented by the chemical formula (a13), and the compound (A5-6) is represented by the chemical formula (a15).

[Chem. 18]

(a14)

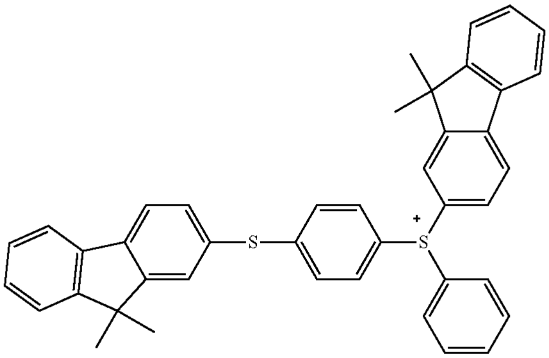

$[(C_3F_7)_3(F)_3P]^-$

[Chem. 19]

(a15)

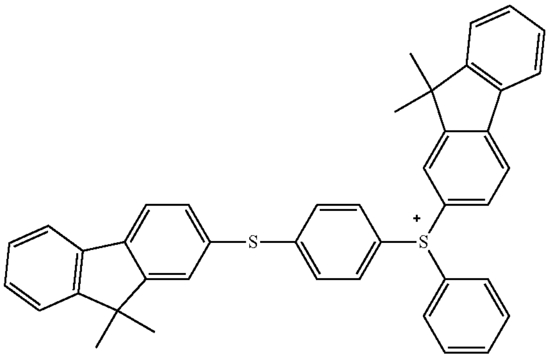

$[(C_6F_5)_3(F)_3P]^-$

Evaluation of Chemically Amplifiable Positive Photoresist Composition

Preparation of Evaluation Sample

As indicated in Table 1, any one of the onium salts (A1-1) to (A1-6), (A2-1) to (A2-6), (A3-1) to (A3-6), (A4-1) to (A4-6), and (A5-1) to (A-8) of the present invention as a photoacid generator in an amount of 1 part by weight, 40 parts by weight of a resin represented by the following formula (Resin-1) as the resin component (F), and 60 parts by weight of a novolac resin as the resin component (G) obtained by addition condensation of m-cresol and p-cresol in the presence of formaldehyde and an acid catalyst were uniformly dissolved in a solvent (propylene glycol monomethylether acetate). The resulting solution was filtered through a membrane filter with a pore size of 1 μm. Thus, chemically amplifiable positive photoresist compositions having a solid concentration of 40% by weight were prepared (Examples P1 to P30). Chemically amplifiable positive photoresist compositions of comparative examples (Comparative Examples P'1 to P'5) were prepared as above using the components in the amounts indicated in Table 1.

TABLE 1

| | Onium salt (A) | Amount of onium salt (A) | Resin (F) | Resin (G) | Solvent |
|---|---|---|---|---|---|
| Example | | | | | |
| P1 | A1-1 | 1 | 40 | 60 | 150 |
| P2 | A1-2 | 1 | 40 | 60 | 150 |
| P3 | A1-3 | 1 | 40 | 60 | 150 |
| P4 | A1-4 | 1 | 40 | 60 | 150 |
| P5 | A1-5 | 1 | 40 | 60 | 150 |
| P6 | A1-6 | 1 | 40 | 60 | 150 |
| P7 | A2-1 | 1 | 40 | 60 | 150 |
| P8 | A2-2 | 1 | 40 | 60 | 150 |
| P9 | A2-3 | 1 | 40 | 60 | 150 |
| P10 | A2-4 | 1 | 40 | 60 | 150 |
| P11 | A2-5 | 1 | 40 | 60 | 150 |
| P12 | A2-6 | 1 | 40 | 60 | 150 |
| P13 | A3-1 | 1 | 40 | 60 | 150 |
| P14 | A3-2 | 1 | 40 | 60 | 150 |
| P15 | A3-3 | 1 | 40 | 60 | 150 |
| P16 | A3-4 | 1 | 40 | 60 | 150 |
| P17 | A3-5 | 1 | 40 | 60 | 150 |
| P18 | A3-6 | 1 | 40 | 60 | 150 |
| P19 | A4-1 | 1 | 40 | 60 | 150 |
| P20 | A4-2 | 1 | 40 | 60 | 150 |
| P21 | A4-3 | 1 | 40 | 60 | 150 |
| P22 | A4-4 | 1 | 40 | 60 | 150 |
| P23 | A4-5 | 1 | 40 | 60 | 150 |
| P24 | A4-6 | 1 | 40 | 60 | 150 |
| P25 | A5-1 | 1 | 40 | 60 | 150 |
| P26 | A5-2 | 1 | 40 | 60 | 150 |
| P27 | A5-3 | 1 | 40 | 60 | 150 |
| P28 | A5-4 | 1 | 40 | 60 | 150 |
| P29 | A5-5 | 1 | 40 | 60 | 150 |
| P30 | A5-6 | 1 | 40 | 60 | 150 |
| Comparative Example | | | | | |
| P'1 | A'1-1 | 1 | 40 | 60 | 150 |
| P'2 | A'2-1 | 1 | 40 | 60 | 150 |
| P'3 | A'3-1 | 1 | 40 | 60 | 150 |
| P'4 | A'4-1 | 1 | 40 | 60 | 150 |
| P'5 | A'5-1 | 1 | 40 | 60 | 150 |

[Chem. 20]

(Resin-1)

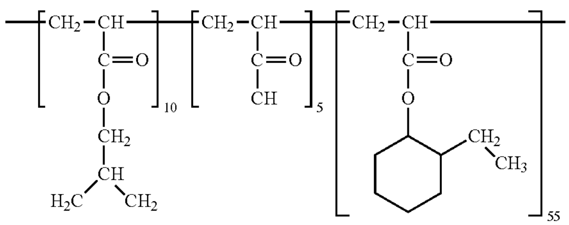

Sensitivity Evaluation

The positive resist compositions prepared in Examples P1 to P30 and Comparative Examples P'1 to P'5 were each spin-coated or a silicon wafer substrate and dried, thereby preparing a photoresist layer having a thickness of about 20 μm. The resist layer was pre-baked on a hot plate at 130° C. for six minutes. After pre-baking, pattern exposure (i-rays) was performed using TME-150RSC (TOPCON CORPORATION), followed by post-exposure baking (PEB) using a hot plate at 75° C. for five minutes. Subsequently, development was performed for five minutes by an immersion method using a 2.38% by weight aqueous solution of tetramethyl ammonium hydroxide. The workpiece was washed with running water and then subjected to nitrogen blowing, thereby forming a 10 μm line-and-space (L&S) pattern. Next, a minimum exposure dose under which no pattern remains, i.e., a minimum required exposure dose (corresponding to sensitivity) needed to form a resist pattern, was measured.

Pattern Shape Evaluation

The cross-sectional shape of the 10 μm-thick L&S pattern formed on the silicon wafer substrate by the above operation was observed, with a scanning electron microscope to measure the length La of the lower side and the length Lb of the upper side. The pattern shape was evaluated based on the following criteria. Table 2 shows the results.

Very good (○○): 0.90≤Lb/La≤1

Good (○): 0.85≤Lb/La<0.90

Bad (x): Lb/La<0.85

TABLE 2

| | Onium salt (A) | Minimum required exposure dose (mJ/cm$^2$) | Pattern shape |
|---|---|---|---|
| Example | | | |
| P1 | A1-1 | 200 | ○○ |
| P2 | A1-2 | 200 | ○○ |
| P3 | A1-3 | 170 | ○○ |
| P4 | A1-4 | 150 | ○○ |
| P5 | A1-5 | 190 | ○○ |
| P6 | A1-6 | 160 | ○○ |
| P7 | A2-1 | 200 | ○○ |
| P8 | A2-2 | 200 | ○○ |
| P9 | A2-3 | 165 | ○○ |
| P10 | A2-4 | 150 | ○○ |
| P11 | A2-5 | 180 | ○○ |
| P12 | A2-6 | 155 | ○○ |
| P13 | A3-1 | 200 | ○○ |
| P14 | A3-2 | 200 | ○○ |
| P15 | A3-3 | 165 | ○○ |
| P16 | A3-4 | 150 | ○○ |
| P17 | A3-5 | 180 | ○○ |
| P18 | A3-6 | 155 | ○○ |
| P19 | A4-1 | 200 | ○○ |
| P20 | A4-2 | 200 | ○○ |
| P21 | A4-3 | 165 | ○○ |
| P22 | A4-4 | 150 | ○○ |
| P23 | A4-5 | 180 | ○○ |
| P24 | A4-6 | 155 | ○○ |
| P25 | A5-1 | 200 | ○○ |
| P26 | A5-2 | 200 | ○○ |
| P27 | A5-3 | 165 | ○○ |
| P28 | A5-4 | 160 | ○○ |
| P29 | A5-5 | 180 | ○○ |
| P30 | A5-6 | 160 | ○○ |
| Comparative Example | | | |
| P'1 | A'1-1 | 270 | ○ |
| P'2 | A'2-1 | 270 | ○ |
| P'3 | A'3-1 | 290 | ○ |
| P'4 | A'4-1 | 255 | ○ |
| P'5 | A'5-1 | 255 | ○ |

As demonstrated in Table 2, the minimum required exposure doses for the chemically amplifiable positive photoresist compositions of Examples P1 to P30 are lower than these of Comparative Examples P'1 to P'5. In other words, the photoacid generator of the present invention is more sensitive than the comparative photoacid generators and is also excellent in pattern shapes.

Evaluation of Chemically Amplifiable Negative Photoresist Composition

<Preparation of Evaluation Sample>

As indicated in Table 3, any one of the onium salts (A1-1) to (A1-6), (A2-1) to (A2-6), (A3-1) to (A3-6), (A4-1) to (A4-6), and (A5-1) to (A-6) of the present invention as a photoacid generator in an amount of 1 part by weight, 100 parts by weight of a copolymer (Mw=10,000) having a molar ratio of p-hydroxystyrene/styrene of 80/20 which is a phenolic resin as the component (I), 20 parts by weight of hexamethoxymethyl melamine (Sanwa Chemical Co., Ltd., trade name "NIKALAC MW-390") which is a crosslinking agent as the component. (J), 10 parts by weight of a copolymer (average particle size=65 nm, Tg=−38° C.) having a ratio of butadiene/acrylonitrile/hydroxybutyl methacrylate/methacrylic acid/divinylbenzene of 64/20/8/6/2 by weight) which is crosslinked fine particles as the component (K), and 5 parts by weight of γ-glycidoxypropyltrimethoxysilane (Chisso Corporation, trade name "S510") which is an adhesion aid were uniformly dissolved in 150 parts by weight of a solvent (ethyl lactate). Thus, chemically amplifiable negative photoresist compositions of the present invention were prepared (Examples N1 to N30). Chemically amplifiable negative photoresist compositions of comparative examples (Comparative Examples N'1 to N'5) were prepared as above using the components in the amounts indicated in Table 3.

TABLE 3

| | Onium salt (A) | Amount of onium salt | Resin (I) | Crosslinking agent (J) | Crosslinked fine particles (K) | Adhesion aid | Solvent |
|---|---|---|---|---|---|---|---|
| Example | | | | | | | |
| N1 | A1-1 | 1 | 100 | 20 | 10 | 5 | 150 |
| N2 | A1-2 | 1 | 100 | 20 | 10 | 5 | 150 |
| N3 | A1-3 | 1 | 100 | 20 | 10 | 5 | 150 |
| N4 | A1-4 | 1 | 100 | 20 | 10 | 5 | 150 |
| N5 | A1-5 | 1 | 100 | 20 | 10 | 5 | 150 |
| N6 | A1-6 | 1 | 100 | 20 | 10 | 5 | 150 |
| N7 | A2-1 | 1 | 100 | 20 | 10 | 5 | 150 |
| N8 | A2-2 | 1 | 100 | 20 | 10 | 5 | 150 |
| N9 | A2-3 | 1 | 100 | 20 | 10 | 5 | 150 |
| N10 | A2-4 | 1 | 100 | 20 | 10 | 5 | 150 |
| N11 | A2-5 | 1 | 100 | 20 | 10 | 5 | 150 |
| N12 | A2-6 | 1 | 100 | 20 | 10 | 5 | 150 |
| N13 | A3-1 | 1 | 100 | 20 | 10 | 5 | 150 |
| N14 | A3-2 | 1 | 100 | 20 | 10 | 5 | 150 |
| N15 | A3-3 | 1 | 100 | 20 | 10 | 5 | 150 |
| N16 | A3-4 | 1 | 100 | 20 | 10 | 5 | 150 |
| N17 | A3-5 | 1 | 100 | 20 | 10 | 5 | 150 |
| N18 | A3-6 | 1 | 100 | 20 | 10 | 5 | 150 |
| N19 | A4-1 | 1 | 100 | 20 | 10 | 5 | 150 |
| N20 | A4-2 | 1 | 100 | 20 | 10 | 5 | 150 |
| N21 | A4-3 | 1 | 100 | 20 | 10 | 5 | 150 |
| N22 | A4-4 | 1 | 100 | 20 | 10 | 5 | 150 |
| N23 | A4-5 | 1 | 100 | 20 | 10 | 5 | 150 |
| N24 | A4-6 | 1 | 100 | 20 | 10 | 5 | 150 |
| N25 | A5-1 | 1 | 100 | 20 | 10 | 5 | 150 |
| N26 | A5-2 | 1 | 100 | 20 | 10 | 5 | 150 |
| N27 | A5-3 | 1 | 100 | 20 | 10 | 5 | 150 |
| N28 | A5-4 | 1 | 100 | 20 | 10 | 5 | 150 |
| N29 | A5-5 | 1 | 100 | 20 | 10 | 5 | 150 |
| N30 | A5-6 | 1 | 100 | 20 | 10 | 5 | 150 |
| Comparative Example | | | | | | | |
| N'1 | A'1-1 | 1 | 100 | 20 | 10 | 5 | 150 |
| N'2 | A'2-1 | 1 | 100 | 20 | 10 | 5 | 150 |
| N'3 | A'3-1 | 1 | 100 | 20 | 10 | 5 | 150 |
| N'4 | A'4-1 | 1 | 100 | 20 | 10 | 5 | 150 |
| N'5 | A'5-1 | 1 | 100 | 20 | 10 | 5 | 150 |

<Sensitivity Evaluation>

Each composition was spin-coated on a silicon wafer substrate and dried by heating at 110° C. for three minutes using a hoc plate, thereby preparing a resin film having a thickness of about 20 μm. Then, pattern exposure (i-rays) was performed using TME-150RSC (TOPCON CORPORATION), followed by post-exposure baking (PEB) using a hot plate at 110° C. for three minutes. Subsequently, development was performed for two minutes by an immersion method using a 2.38% by weight aqueous solution of tetramethyl ammonium hydroxide. The workpiece was washed with running water and then subjected to nitrogen blowing, thereby forming a 10 μm line-and-space pattern. Next, a minimum required exposure dose (corresponding to sensitivity) to form a pattern having a film-remaining ratio of 95% or higher was measured. The film remaining ratio refers to a ratio of the remaining film after development relative to that before development.

Pattern Shape Evaluation

The cross-sectional shape of the 20 μm-thick L&S pattern formed on the silicon wafer substrate by the above operation was observed with a scanning electron microscope to measure the length La of the lower side and the length Lb of the upper side. The pattern shape was evaluated based on the following criteria. Table 6 shows the results.

Very good (○○): 0.90≤La/Lb≤1
Good (○): 0.35≤La/Lb<0.90
Bad (x): La/Lb<0.85

TABLE 4

| | Onium salt (A) | Minimum required exposure dose ($mJ/cm^2$) | Pattern shape |
|---|---|---|---|
| Example | | | |
| N1 | A1-1 | 180 | ○○ |
| N2 | A1-2 | 180 | ○○ |
| N3 | A1-3 | 140 | ○○ |
| N4 | A1-4 | 120 | ○○ |
| N5 | A1-5 | 170 | ○○ |
| N6 | A1-6 | 160 | ○○ |
| N7 | A2-1 | 180 | ○○ |
| N8 | A2-2 | 180 | ○○ |
| N9 | A2-3 | 140 | ○○ |
| N10 | A2-4 | 110 | ○○ |
| N11 | A2-5 | 170 | ○○ |
| N12 | A2-6 | 160 | ○○ |
| N13 | A3-1 | 185 | ○○ |
| N14 | A3-2 | 180 | ○○ |
| N15 | A3-3 | 140 | ○○ |
| N16 | A3-4 | 120 | ○○ |
| N17 | A3-5 | 170 | ○○ |
| N18 | A3-6 | 160 | ○○ |
| N19 | A4-1 | 170 | ○○ |
| N20 | A4-2 | 170 | ○○ |
| N21 | A4-3 | 130 | ○○ |
| N22 | A4-4 | 115 | ○○ |
| N23 | A4-5 | 160 | ○○ |
| N24 | A4-6 | 150 | ○○ |
| N25 | A5-1 | 165 | ○○ |
| N26 | A5-2 | 165 | ○○ |
| N27 | A5-3 | 130 | ○○ |
| N28 | A5-4 | 120 | ○○ |
| N29 | A5-5 | 165 | ○○ |
| N30 | A5-6 | 155 | ○○ |
| Comparative Example | | | |
| N'1 | A'1-1 | 250 | ○ |
| N'2 | A'2-1 | 255 | ○ |
| N'3 | A'3-1 | 255 | ○ |
| N'4 | A'4-1 | 240 | ○ |
| N'5 | A'5-1 | 240 | ○ |

As demonstrated in Table 4, the minimum required exposure doses for the chemically amplifiable negative photoresist compositions of Examples N1 to N38 are lower than those of Comparative Examples N'3 to N'5. In other words, the photoacid generator of the present invention is more sensitive than the comparative photoacid generators and is also excellent in pattern shapes.

INDUSTRIAL APPLICABILITY

The chemically amplifiable positive photoresist compositions and the chemically amplifiable negative photoresist compositions each containing an acid generator that contains the onium salt of the present invention can form a highly sensitive resist (i.e., enable pattern formation with a lower exposure than conventional ones). Furthermore, the chemically amplifiable positive photoresist, compositions and the chemically amplifiable negative photoresist compositions of the present invention form good resist patterns.

The invention claimed is:

1. A chemically amplifiable resist composition comprising:

an onium salt represented by formula (1), $$[(R^2)_{n+1}\text{-}E]^+[(R^1)_3(F)_3P]^- \quad (1),$$

wherein:

$R^1$ is a halogen-substituted C1-C18 alkyl group or a C6-C18 (excluding the carbon number of the following substituents) aryl group, with at least one hydrogen in the aryl group being optionally replaced by a C1-C18 alkyl group, a halogen atom, a halogen-substituted C1-C8 alkyl group, a C2-C18 alkenyl group, or a C2-C18 alkynyl group;

E is S or I with a valence of n;

n is an integer of 1 to 3; and $R^2$ is an organic group attached to the E, with the number of $R^2$s being n+1, these $R^2$s being the same as or different from each other, and two or more $R^2$s being optionally attached to each other directly or with —O—, —S—, —SO—, —$SO_2$—, —NH—, —CO—, —COO—, —CONH—, an alkylene group, or a phenylene group in between to form a ring structure containing the E, and wherein the onium salt represented by formula (1) comprises an anion structure with a proportion of a facial isomer in a total of the facial isomer and a meridional isomer of 15.0% by weight or lower.

2. The chemically amplifiable resist composition according to claim 1, wherein the proportion of the facial isomer is 0.1 to 15.0% by weight.

3. The chemically amplifiable resist composition according to claim 1, wherein $R^1$ in the formula (1) is a perfluoroalkyl group or a fluorine-substituted phenyl group.

* * * * *